(12) United States Patent
Redfield et al.

(10) Patent No.: US 7,863,242 B2
(45) Date of Patent: Jan. 4, 2011

(54) COMPOSITIONS FOR DOWN-REGULATION OF CCR5 EXPRESSION AND METHODS OF USE THEREOF

(75) Inventors: Robert R. Redfield, Baltimore, MD (US); Anthony Amoroso, Baltimore, MD (US); Charles E. Davis, Laurel, MD (US); Alonso Heredia, Washington, DC (US)

(73) Assignee: University of Maryland, Baltimore, Baltimore, MD (US)

( * ) Notice: Subject to any disclaimer, the term of this patent is extended or adjusted under 35 U.S.C. 154(b) by 1038 days.

(21) Appl. No.: 11/281,195

(22) Filed: Nov. 16, 2005

(65) Prior Publication Data
US 2006/0154857 A1    Jul. 13, 2006

Related U.S. Application Data

(63) Continuation-in-part of application No. PCT/US2004/015681, filed on May 17, 2004.

(60) Provisional application No. 60/471,453, filed on May 16, 2003.

(51) Int. Cl.
- *A61K 38/00* (2006.01)
- *A61K 31/445* (2006.01)
- *A61K 31/33* (2006.01)

(52) U.S. Cl. .................. 514/12; 514/315; 514/183
(58) Field of Classification Search .......... 514/12, 514/185, 315
See application file for complete search history.

(56) References Cited

U.S. PATENT DOCUMENTS

| 5,962,462 | A | 10/1999 | Mills et al. |
|---|---|---|---|
| 5,994,136 | A | 11/1999 | Naldini |
| 6,013,644 | A | 1/2000 | Mills et al. |
| 6,098,780 | A | 8/2000 | Kelly et al. |
| 6,150,530 | A | 11/2000 | Kempf et al. |
| 2003/0060457 | A1 | 3/2003 | Schaffer et al. |
| 2003/0099944 | A1 | 5/2003 | Schaffer et al. |
| 2006/0099170 | A1 | 5/2006 | Redfield et al. |

FOREIGN PATENT DOCUMENTS

| WO | WO-94/05300 A1 | 3/1994 |
|---|---|---|
| WO | WO98/25604 | 12/1997 |

(Continued)

OTHER PUBLICATIONS

Lori, et al. "Strucutured treatment interruptions as a potential alternative therapeutic regimen", Journal of Antimicrobial Chaemotherapy (2002) 50, 155-160.

(Continued)

Primary Examiner—Shengjun Wang
(74) Attorney, Agent, or Firm—Marianne Fuierer; Moore & Van Allen, PLLC

(57) ABSTRACT

The present invention relates to the downregulation of surface receptor CCR5 expression through manipulation of the cell cycle in activated lymphocytes by administering a composition that arrests the G1 phase of the cell cycle, thereby reducing receptor sites for entry of HIV into T cells, and thus, the effects of HIV. Further, compositions are disclosed that include at least one G1 phase arresting agent and at least one antiviral agent, wherein the combination of agents synergistically enhances the activity of the antiviral agent.

2 Claims, 19 Drawing Sheets

FOREIGN PATENT DOCUMENTS

| WO | WO-99/47146 A1 | 9/1999 |
| --- | --- | --- |
| WO | WO-99/48504 A1 | 9/1999 |
| WO | WO00/51610 | 3/2000 |
| WO | WO 02/053096 | 7/2002 |
| WO | WO 02/056902 A2 * | 7/2002 |
| WO | WO 02/062123 | 8/2002 |
| WO | WO03/027671 | 9/2002 |
| WO | WO02100401 | 12/2002 |
| WO | WO 03/053468 | 7/2003 |

OTHER PUBLICATIONS

Spada, et al. "An Evaluation of Antiretrovial Therapy Associated with α-Tocopherol" Clin. Chem.. Lab. Med (2002) 40(5), 456-459.

Paton, et al., "Hydroxychloroquine, hydroxycarbamide and didanosine as economic treatment for HIV-1" The Lancet, (2002) V.359, 1667.

Baba, M., Nishimura, O., Kanzaki, N., Okamoto, M., Sawada, H., Iizawa, Y., Shiraishi, M., Aramaki, Y., Okonogi, K., Ogawa, Y., et al. (1999) *Proc. Natl. Acad. Sci. USA* 96, 5698-5703.

Baba, M., Imai, T., Yoshida, T. & Yoshie, O. (1996) *Int. J. Cancer* 66, 124-129.

Bleul, C., Wu, L., Hoxie, J., Springer, T. & Mackay, C. (1997) *Proc. Natl. Acad. Sci. USA* 94, 1925-1930.

Bjornal, A., Sonnerborg, A., Tscherning, C., Albert, J. & Fenyo, E. (1999) *AIDS Res. Hum. Retroviruses* 15, 647-653.

Calabrese, L., Lederman, M., Spritzler, J., Coombs, R., Fox, L., Schock, B., Yen-Lieberman, B., Johnson, R., Mildvan, D. & Parekh, N. (2002) *J. Acquired Immune Defic. Syndr.* 29, 356-362.

Cocchi, F., DeVico, A., Garzino-Demo, A., Arya, S., Gallo, R. & Lusso, P. (1995) *Science* 270, 1811-1815.

Castedo, et al., (2002) EMBO Journal, 21 (15) pp. 4070-4080.

Dybul, M., Fauci, A., Barlett, J., Kaplan, J. & Pau, A. (2002) *Ann. Intern. Med.* 137, 381-433.

Essex, M. (1999) *Adv. Virus Res.* 53, 71-88.

Guba, M., von Breitenbuch, P., Steinbauer, M., Koehl, G., Flegel, S., Hornung, M., Bruns, C. J., Zuelke, C., Farkas, S., Anthuber, M., et al. (2002) *Nat. Med.* 8, 128-135.

Heredia, A; Amoroso, A; Davis, C.; Le, N.; Readon, E.; Klingebiel, E.; Gallo, R.C; and Redfield R.R. (2003) *Proc. Natl. Acad. Sci. USA*, 100 (18) 10411-10416.

Heredia, A., Davis, C., Amoroso, A., Dominique, J., Le, N., Klingebiel, E., Reardon, E., Zella, D. & Redfield, R. (2003) *Proc. Natl. Acad. Sci. USA* 100, 4179-4184.

Heredia, A. et al, Journal of Human Virology 3(5): 248 (Sep.-Oct. 2000).

Kahan, B. & Camardo, J. (2001) *Transplantation* 72, 1181-1193.

Kinter, A., Poli, G., Fox, L., Hardy, E. & Fauci, A. (1995) *J. Immunol.* 154, 2448-2459.

Lane, B., Markovitz, D., Woodford, N., Rochford, R., Strieter, R. & Coffey, M. (1999) *J. Immunol.* 163, 3653-3661.

Levine, B., Mosca, J., Riley, J., Carroll, R. G., Vahey, M. T., Jagodzinski, L. L., Wagner, K. F., Mayers, D. L., Burke, D. S., Weislow, O. S., et al. (1996) *Science* 272, 1939-1943.

Liu, R., Paxton, W., Choe, S., Ceradini, D., Martin, S., Horuk, R., MacDonald, M., Stuhlmann, H., Koup, R. & Landau, N. (1996) *Cell* 86, 367-377.

Lin, Y.-L., Mettling, C., Portales, P., Reynes, J., Clot, J. & Corbeau, P. (2002) *Proc. Natl. Acad. Sci. USA* 99, 15590-15595.

Loetscher, P., Seitz, M., Baggiolini, M. & Moser, B. (1996) *J. Exp. Med.* 184, 569-577.

Lori, F., Malykh, A., Cara, A., Sun, D., Weinstein, J. N., Lisziewicz, J. & Gallo, R. C. (1994) *Science* 266, 801-805.

Morice, et al. (1993) *J. Biological Chemistry*, vol. 268 (5) pp. 3734-3738.

Perno, C. & Yarchoan, R. (1993) in *Current Protocols in Immunology*, eds. Coligan, J. E., Kruisbeek, A. M., Margulies, D. H., Shevach, E. M. & Strober, W. (Wiley, New York), pp. 12.4.1-12.4.11.

Poli, G. & Fauci, A. (1993) in *Current Protocols in Immunology*, eds. Coligan, J. E., Kruisbeek, A. M., Margulies, D. H., Shevach, E. M. & Strober, W. (Wiley, New York), pp. 12.3.1-12.3.7.

Poon, M., Badimon, J. & Fuster, V. (2002) *Lancet* 359, 619-622.

Reeves J et al., (2002) PNAS 99: 16249-16254.

Rizzardi, G., Harari, A., Capiluppi, B., Tambussi, G., Ellefsen, K., Ciuffreda, D., Champagne, P., Bart, P., Chave, J., Lazzarin, A. & Pantaleo, G. (2002) *Clin. Invest.* 109, 681-688.

Roy, J., Sébastien, J., Fortin, J. & Tremblay, M. (2002) *Antimicrob. Agents Chemother.* 46, 3447-3455.

Sehgal, S.-N. (1998) *Clin. Biochem.* 31, 335-340.

Simmons, G., Clapham, P., Picard, L., Offord, R. E., Rosenkilde, M. M., Schwartz, T. W., Buser, R., Wells, T. N. & Proudfoot, A. E. (1997) *Science* 276, 276-279.

Spina, C., Guatelli, J. & Richman, D. (1995) *J. Virol.* 69, 2977-2988.

Strizki, J., Xu, S., Wagner, N., Wojcik, L., Liu, J., Hou, Y., Endres, M., Palani, A., Shapiro, S., Clader, J. W., et al. (2001) *Proc. Natl. Sci. USA* 98, 12718-12723.

Trkola, A., Kuhmann, S., Strizki, J., Maxwell, E., Ketas, T., Morgan, T., Pugach, P., Xu, S., Wojcik, L., Tagat, J., et al. (2002) *Proc. Natl. Acad. Sci. USA* 99, 395-400.

Terada N, et al., (1993) J of Cellular Phys., 154 pp. 7-15.

Ullman, K., Northrop, J., Verweij, C. & Crabtree, G. (1990) *Annu. Rev. Immunol.* 8, 421-452.

Ward, S., Bacon, K. & Westick, J. (1998) *Immunity* 9, 1-11.

Weissman, D., Dybul, M., Daucher, M., Davey, R., Walker, R. & Kovacs, J. (2000) *J. Infect. Dis.* 181, 933-938.

Willey, R., Smith, D., Lasky, L., Theodore, T., Earl, P., Moss, B., Capon, D. & Martin, M. (1988) *J. Virol.* 62, 139-147.

Zack, J., Arrigo, S., Weitsman, S., Go, A., Haislip, A. & Chen, I. (1990) *Cell* 61, 213-222.

Zella, D., Riva, A., Weichold, F., Reitz, M. & Gerna, G. (1998) *Immunol. Lett.* 62, 45-49.

Andrieu, et al. "Results of a 2-year exploratory study with cyclosporin a in human immunodeficiency virus infection." (1998) in *Autoimmune Aspects of HIV Infection*, eds. (R. Soc. Med. Services, London), pp. 191-194.

Sherman DS. Et al, "Hydroxurea in the treatment of HIV infection" AIDS Reader, vol. 9, No. 1, Jan. 1999, pp. 18-19 and 23-24.

Kootstra NA, et al. "Diminished human immunodeficiency virus type 1 reverse transcription and nuclear transpro in primary macrophages arrested in early G1 phase of the cell cycle" Journal of Virology, vol. 74, No. 4, Feb. 2000, pp. 1712-1717.

Wang et al, "Inhibition of Human Immunodeficiency Virus Type 1 Transcription by Chemical Cyclin-Dependent Kinase Inhibitors" Journal of Virology, The American Society for Microbiology, vol. 75, No. 16. Aug. 2001, pp. 7266-7279.

* cited by examiner

COMPOSITIONS FOR DOWN-REGULATION OF CCR5 EXPRESSION AND METHODS OF USE THEREOF

CROSS REFERENCE TO RELATED APPLICATIONS

This application is a Continuation-in-Part application of and claims priority to PCT International Application No: PCT/US2004/015681 filed on May 17, 2004, which in turn claims priority to U.S. Provisional Application No. 60/471,453 filed on May 16, 2003, the contents of which are incorporated herein for reference for all purposes.

BACKGROUND OF THE INVENTION

1. Field of the Invention

The present invention generally relates to down-regulation of CCR5 expression, and more particularly, to compositions comprising at least one G1 phase arresting agent that exhibits down-regulation of surface receptor CCR5 expression thereby treating human diseases in which CCR5 receptors plays an adverse role.

2. Background of the Related Art

The human immunodeficiency virus (HIV) has been implicated as the primary cause of the slowly degenerative immune system disease termed acquired immune deficiency syndrome (AIDS). There are at least two distinct types of HIV: HIV-1 and HIV-2. In humans, HIV replication occurs prominently in CD4 T lymphocyte populations, and HIV infection leads to depletion of this cell type and eventually to immune incompetence, opportunistic infections, neurological dysfunctions, neoplastic growth, and ultimately death.

HIV is a member of the lentivirus family of retroviruses. Retroviruses are small-enveloped viruses that contain a single-stranded RNA genome, and replicate via a DNA intermediate produced by a virally encoded reverse transcriptase, an RNA-dependent DNA polymerase.

The HIV viral particle comprises a viral core, composed in part of capsid proteins, together with the viral RNA genome and those enzymes required for early replicative events. Myristylated gag protein forms an outer shell around the viral core, which is, in turn, surrounded by a lipid membrane envelope derived from the infected cell membrane. The HIV envelope surface glycoproteins are synthesized as a single 160 kilodalton precursor protein, which is cleaved by a cellular protease during viral budding into two glycoproteins, gp41 and gp120. gp41 is a transmembrane glycoprotein and gp120 is an extracellular glycoprotein, which remains non-covalently associated with gp41, possibly in a trimeric or multimeric form.

HIV is targeted to CD4 cells because a CD4 cell surface protein (CD4) acts as the cellular receptor for the HIV-1 virus. Viral entry into cells is dependent upon gp120 binding the cellular CD4 receptor molecules, explaining HIV's tropism for CD4 cells, while gp41 anchors the envelope glycoprotein complex in the viral membrane. CCR5 serves as a co-receptor for the infection of CD4 cells by nonsyncytium-inducing (NSI) strains of HIV-1.

Expression of the CCR5 receptor on T cells is dependent on the activation state of the cells. Resting lymphocytes do not express CCR5, however, upon activation, CCR5 is expressed. The importance of CCR5 for initial transmission of HIV-1 is highlighted by the fact that individuals lacking expression of CCR5 (the CCR5-Δ32 homozygous genotype) are usually resistant to infection (Liu, et al., 1996). In addition, recent studies show that CCR5 cell-surface density correlates with disease progression in infected individuals (Lin, et al., 2002).

Other disorders and the progression of effects have been found to be related to expression of the CCR5 receptor. For example, allograft rejection occurs as a result of extravasation of recipient mononuclear cells into the allograft, a process that is mediated by expression of CCR5 on the infiltrating mononuclear cells. Asthma studies using murine models of allergic airway disease have shown that CCR5 likely plays an important role in airway inflammation. Further, rheumatoid arthritis is characterized by the infiltration of the synovial membrane with mononuclear cells and CCR5 seems to play a role due to the high levels of CCR5 expression found in infiltrated lymphocytes. Interestingly, mononuclear cells present in the active demyelinating plaques characteristic of subject suffering from multiple sclerosis also show high levels of CCR5 expression.

Thus, it would be advantageous to identify compounds that reduce or inhibit the expression of CCR5 surface receptors on mononuclear cells and administer such compounds to effect treatment of disorders related to the expression of CCR5 surface receptors.

SUMMARY OF THE INVENTION

The present invention relates to the downregulation of surface receptor CCR5 expression through manipulation of the cell cycle in activated lymphocytes by administering a composition that arrests the G1 phase of the cell cycle, thereby disrupting the response of a lymphocyte to IL-2 (through the IL-2R) which governs the transition from G1 to S phase, as well as the progression through S phase. The reduction of the CCR5 expression reduces receptor sites for entry of HIV into T cells, and thus, the effects of HIV progression.

In one aspect, the present invention relates to suppressing transcription of CCR5, to reduce expression of CCR5 surface receptors thereby causing an accumulation of chemokines at the cellular level. This accumulation of chemokines is due to reduced number of surface CCR5 receptors for chemokine/ligand uptake.

In another aspect, the present invention relates to suppressing transcription of CCR5, to reduce expression of CCR5 surface receptors thereby causing a reduced number of surface receptors for binding of HIV gp120, which, in turn, prevents or reduces replication of HIV.

In another aspect, the present invention relates to compositions that inhibit CCR5-mediated viral entry of HIV by decreasing the number of CCR5 surface receptors expressed on mononuclear cells including, but not limited to T cells, activated T cells and macrophages.

In another aspect, the invention relates to a composition comprising a G1 phase arresting agent that delays entry of the S-phase in a mononuclear cell cycle, wherein the G1 phase arresting agent disrupts signals occurring after binding of IL-2 to the IL-2 receptor (IL-2R) on the cell surface and thus suppresses the expression of CCR5 which is dependent on signaling through the IL-2 receptor.

Still another aspect of the present invention relates to a method for inhibiting CCR5-mediated viral entry, namely the downregulation of CCR5 protein expression by the immuno-modulatory drug rapamycin (RAPA). RAPA, a bacterial macrolide that is currently approved for the treatment of renal transplantation rejection, exerts cytostatic activity in T cells by disrupting molecular events resulting from the binding of IL-2 to the IL-2 receptor (Sehgal, S. N., 1998).

The G1 cell cycle modulating agent may include any compound that arrests or prolongs the G1 phase in the cell cycle of mononuclear cells, for example, including but not limited to sodium butyrate, aphidicolin, hydroxyurea (HU), olomoucine, roscovitine, tocopherols, including alpha-tocopherol, beta-tocopherol, D-alpha-tocopherol, delta-tocopherol, gamma-tocopherol, tocotrienols, indirubin-3'-monoxime, rapamycin (RAPA) and functional analogs or derivatives thereof.

The compositions of the present invention may further comprise at least one antiviral agent. The antiviral agent may include any agent that inhibits entry into a cell or replication therein of an infectious virus, and specifically retroviruses, such as HIV viruses. The antiviral agents include, but are not limited to nucleoside RT inhibitors, CCR5 inhibitors/antagonists, viral entry inhibitors and their functional analogs.

Thus, in one aspect the compositions and methods of the present invention further comprise a therapeutically effective amount of at least one antiviral agent, including, but not limited to: nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies;

viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

Another aspect of the present invention relates to a method to enhance the efficacy of TAK-779 and decrease the number of CCR5 surface receptors on an activated T cell, the method comprising:
administering a composition comprising: a) TAK-779 in an amount found to be ineffective in antagonizing CCR5 receptors and b) a G1 phase arresting agent in an amount effective to reduce expression of CCR5, whereby the inclusion of the G1 phase arresting agent in the composition increases the efficacy of TAK-779. Preferably, the G1 phase arresting agent is RAPA or HU and the efficacy is synergistically increased.

TAK-779 is a nonpeptide compound with a small molecular weight ($M_r$ 531.13), having an IUPAC name of N,N-dimethyl-N-[4-[[[2-(4-methylphenyl)-6,7-dihydro-5H-benzocyclohepten-8-yl]carbonyl]amino]benzyl]tetrahydro-2H-pyran-4-aminium chloride.

In still another aspect, the present invention relates to a method of combating a virus infection wherein CCR5 surface receptor plays an adverse role, comprising:
administering to a patient a composition comprising an effective amount of a G1 phase arresting compound to reduce expression of CCR5 surface receptors.

In yet another aspect, the present invention relates to a method of maintaining durable viral control of HIV, the method comprising:
administering at least one antiviral agent and a G1 phase arresting compound in a therapeutically effective amount to reduce expression of CCR5 receptors thereby reducing binding of HIV gp120.

The antiviral agent may be any HIV entry inhibitor, such as TAK 799 or SCH-C both of which block viral binding to CCR5 receptors. Viral resistance to these CCR5 antagonist molecules has been shown to result from more efficient use of CCR5 by the virus (Trkola, et al., 2002). The fact that HIV-1 viruses are resistant to CCR5 blockers yet still dependant on CCR5 receptors for infection suggests that a decrease in CCR5 will interfere with the growth and emergence of resistant viral variants, thereby increasing the antiviral durability of entry inhibitor therapy.

Another aspect of the present invention relates to a therapeutic method to reduce effects and replication of HIV in a HIV infected subject, the method comprising administering a G1 phase arresting agent in combination with the CCR5 antagonist TAK 779 to synergistically enhance the efficacy of TAK-779 and a reduction of CCR5 expression.

In still a further aspect, the present invention relates to a method of inhibiting HIV in a subject potentially exposed to the HIV, the method comprising:
administering to the subject at least one G1 phase arresting compound in an effective amount to decrease transcription of CCR5 surface receptors thereby inhibiting HIV viral entry into the subject.

Another aspect of the present invention relates to a method of reducing HIV replication in activated lymphocytes, the method comprising:
administering a composition comprising rapamycin and Enfuvirtide in amounts to form a synergistically effective mixture to reduce replication of HIV. Enfuvirtide (T-20) is a synthetic peptide derived from a naturally occurring amino acid sequence known as heptad repeat 2 (HR2) found in gp41, a viral transmembrane glycoprotein that facilitates fusion with host cells.

Other features and advantages of the invention will be apparent from the following detailed description, drawings and claims.

DETAILED DESCRIPTION OF PREFERRED EMBODIMENTS

Figure 1:
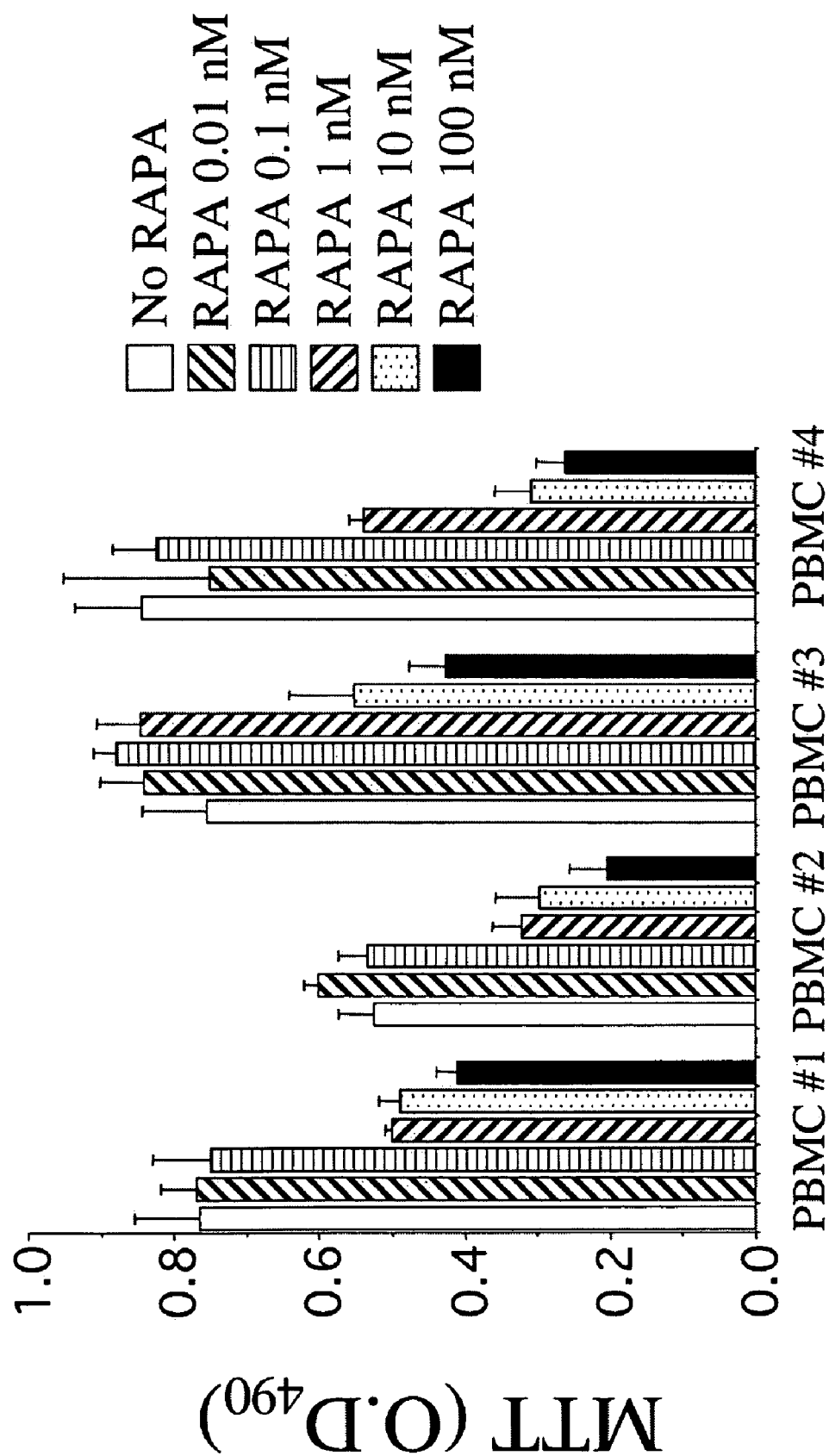
FIG. 1 shows the effect of RAPA on proliferation of PBMCs and reduction of proliferation was noticeable at values greater than 1 nM of RAPA.

A method of treating a viral infection is meant herein to include "prophylactic" treatment or "therapeutic" treatment. A "prophylactic" treatment is a treatment administered to a subject who does not exhibit signs of a disease or who exhibits early signs of the disease for the purpose of decreasing the risk of developing pathology associated with the disease.

The term "therapeutic," as used herein, means a treatment administered to a subject who exhibits signs of pathology for the purpose of diminishing or eliminating those signs.

The term "therapeutically effective amount," as used herein means an amount of compound that is sufficient to provide a beneficial effect to the subject to which the compound is administered. A beneficial effect means rendering a virus incompetent for replication, inhibition of viral replication, inhibition of infection of a further host cell, or increasing CD4 T-cell count, for example.

The term "a virally-targeted cell," as used herein, means a cell in which virus is present and is infective or potentially infective and includes epithelial cells, nervous system cells, T-lymphocytes (activated or resting), macrophage, monocytes, tissue dendritic cells or the like.

The term "functional equivalent," as used herein, means that the agent retains some or all of the biological activity of the corresponding compound.

The term "functional analog," as used herein means compounds derived from a particular parent compound by straightforward substitutions that do not result in a substantial (i.e. more than 100×) loss in the biological activity of the parent compound, where such substitutions are modifications well-known to those skilled in the art, e.g., esterification, replacement of hydrogen by halogen, replacement of alkoxy by alkyl, replacement of alkyl by alkoxy, etc.

The Invention:

G1 Phase Arresting Compounds

The compositions of the present invention may include any G1 phase arresting agent that arrests, delays or prolongs cell-cycle activity in the G1 phase and/or G1-S interface of mononuclear cells and reduces expression of CCR5. Preferably, G1 phase arresting agent disrupts the response of a lymphocyte to IL-2 (through the IL-2R) which governs the transition from G1 to S phase, as well as the progression through S phase.

G1 phase arresting agents may include, but are not limited to, sodium butyrate, aphidicolin, hydroxyurea (HU), olomoucine, roscovitine, tocopherols, tocotrienols, indirubin-3'-monoxime, rapamycin (RAPA) and/or functional analogs thereof. Preferably, the composition comprises rapamycin which inhibits the T cell response to IL-2, the substance which triggers T cells already activated by the TCR to progress through G1. Rapamycin therefore stops the cell at the G1-S transition. More preferably, the composition comprises an effective amount of RAPA to disrupt the response of a lymphocyte to IL-2 (through the IL-2R) which governs the transition from G1 to S phase thereby causing a reduction of CCR5 expression and concomitantly reducing receptor sites for entry of HIV.

The present invention employs one of the above-identified G1 phase arresting compound for administration to a subject suffering from a viral infection, wherein the compound prolongs the G1 phase of the cell cycle of an activated lymphocyte thereby inhibiting expression of CCR5 receptors and reducing binding sites for HIV gp120 ligands.

Pharmaceutical Compositions

The present invention provides compositions comprising at least one G1 phase arresting compound and optionally at least one antiviral agent, as well as methods of preventing, treating and/or reducing the effects of HIV. The methods comprise administering said compositions comprising the G1 phase arresting compounds and optionally antiviral agents, wherein the two compounds can be administered, separately, simultaneously, concurrently or sequentially.

Pharmaceutically Acceptable Derivatives and Salts

The term "pharmaceutically acceptable derivative" is used herein to denote any pharmaceutically or pharmacologically acceptable salt, ester or salt of such ester of a compound according to the invention, or any compound which, upon administration to the recipient, is capable of providing (directly or indirectly) one or more of the compounds according to the invention, or an antivirally active metabolite or residue thereof.

Preferred esters of the G1 phase arresting compounds of the invention include carboxylic acid esters in which the non-carbonyl moiety of the ester grouping is selected from straight or branched chain alkyl. e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$alkyl or $C_{1-4}$ alkoxy or amino); sulfonate esters such as alkyl- or aralkylsulfonyl (e.g. methanesulfonyl); amino add esters (e.g. L-valyl or L-isoleucyl); and mono-, di- or triphosphate esters. The phosphate esters may be further esterified by, for example, a $C_{1-20}$ alcohol or reactive derivative thereof, or by a 2,3-di $C_{2-4}$ acyl glycerol.

Pharmaceutically acceptable salts include, without limitation, salts of organic carboxylic acids such as acetic, lactic, tartaric, malic, isethionic, lactobionic, p-aminobenzoic and succinic acids; organic sulfonic acids such as methanesulfonic, ethanesulfonic, benzenesulfonic and p-toluenesulfonic acids and inorganic adds such as hydrochloric, sulfuric, phosphoric and sulfamic acids.

Anti-Viral Compounds

In one aspect, the compositions and methods of the present invention further comprise a therapeutically effective amount of at least one antiviral agent, including, but not limited to nucleoside RT inhibitors, CCR5 inhibitors/antagonists, viral entry inhibitors and functional analogs thereof.

Preferably, the antiviral agent comprises nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies;

viral entry inhibitors, such as Fuzeon (T-20), NB-2, NB-64, T-649, T-1249, SCH-C, SCH-D, PRO 140, TAK 779, TAK-220, RANTES analogs, AK602, UK-427, 857; and functional analogs thereof.

Antiviral Therapy

Although current treatment with antiretroviral (ARV) therapy causes suppression of HIV replication and results in improvements of immune function, it is limited by high costs, toxicities and adherence difficulties. Moreover, the chance of achieving long-term control of HIV infection with antiretroviral therapy alone seems very unlikely. To date, current antiretroviral therapy has been shown to be insufficient to completely eradicate HIV from infected individuals and there is no real data that the amount of residual virus is decreasing with time on typical antiretroviral therapy. Further, after stopping antiretroviral therapy, the viral load can rebound to higher levels than pretreatment viral loads (Davey, 1999; Dybul, et al., 2002 and 2001).

Antiretroviral therapy demands stringent adherence to complex dosing regimens. The rate of virological failure over a 6-month period of time has been demonstrated to be as high as 60% in patients that cannot achieve greater then 95% adherence. The combination of multiple adverse side effects associated with antiretroviral therapy and the availability of this treatment to only 1 in 20 of the estimated 33 million people infected world wide has prompted reconsideration of the current strategies for achieving the goals of HIV therapy.

Moreover, HIV therapy is now thought to be a life-long process. Therefore, it is crucial to develop effective treatments that can be successfully administered for long periods of time for the suppression of retroviruses, and in particular, the prevention and/or inhibition of HIV. Further, it is desirable to eliminate, or at least minimize, the cytotoxicity associated with the administration of antiviral agents otherwise determined to be effective. It is generally recognized that the toxicity of an antiviral agent may be avoided or at least minimized by administration of a reduced dose of the antiviral agent; however, it is also recognized that the effectiveness of an antiviral agent generally decreases as the dose is reduced.

Thus, one embodiment of the present invention provides for reducing the dose of antiviral agents while maintaining or reducing viral load by using cyclic therapy and introducing the G1 cell cycle agents of the present invention to a dosing regime for an HIV infected subject. Specifically, the use of the G1 phase arresting compounds in combination with antiviral agents has shown promise to maintain viral suppression in a cycle therapy dosing program. By using 50% less medication, side effects associated with antiretroviral use have been shown to be reduced and adherence has shown to be increased. The other obvious impact is on overall cost of medications, which will facilitate expanding these drugs throughout the developed world.

Thus, in one embodiment of the present invention, cyclic therapy is employed as an alternative approach designed to increase activity of antiviral agents, decrease drug cost and toxicity. Furthermore, since one component of the compositions of the present invention targets cellular machinery of the host, rather than the virus, the present inventors expect that viral resistance to this drug combination essentially would not occur.

A cycle antiviral therapy regime can run for about 12 weeks and then a G1 phase arresting compound is added or substituted for four weeks. If the viral load remains low or approximately constant, the cycles can be altered to reduce the time period of each cycle. The time period for consumption of the antiviral drugs can be reduced, if augmented with a G1 phase arresting compound. Furthermore, a time period can be introduced that includes no antiviral drugs and only a G1 phase arresting compound. This time period wherein no antiviral agents are consumed by the subject, provides the biological system of the subject sufficient time to repair or compensate for the toxic effects of the antiviral compound.

Further, the compositions and methods of the present invention can be used to treat HIV viral infections by reducing viral load and replication of the virus by reducing binding sites for gp120 ligands.

Doses to be administered are variable according to the G1 phase arresting agent, the antiviral agent, the treatment period, frequency of administration, the host, and the nature and severity of the infection. The dose can be determined by one of skilled in the art without an undue amount of experimentation.

The compositions of the invention are administered in substantially non-toxic dosage concentrations sufficient to ensure the release of a sufficient dosage unit of the present combination into the patient to provide the desired inhibition of the HIV virus. The actual dosage administered will be determined by physical and physiological factors such as age, body weight, severity of condition, and/or clinical history of the patient. The active antiviral components are ideally administered to achieve in vivo plasma concentrations of an antiviral agent of about 0.01 uM to about 100 uM, more preferably about 0.1 to 10 uM, and most preferably about 1-5 uM, and of a G1 phase arresting agent of about 1 uM-25 uM, more preferably about 2-20 uM, and most preferably about 5-10 uM.

For example, in the treatment of HIV-positive and AIDS patients, the methods of the present invention may use compositions to provide from about 0.005-500 mg/kg body weight/day of an antiviral agent, more preferably from about 0.1-200 mg/kg/day, and most preferably 1-50 mg/kg/day; and from about 0.01-1000 mg/kg body weight/day of a G1 phase arresting agent, more preferably from about 0.001-1000 mg/kg/day, or most preferably from about 0.5-50 mg/kg/day. Particular unit dosages of a G1 phase arresting agent and an antiviral agent of the present invention include 50 mg, 100 mg, 200 mg, 500 mg, and 1000 mg amounts, for example, formulated separately, or together as discussed infra.

It will be understood, however, that dosage levels that deviate from the ranges provided may also be suitable in the treatment of a given viral infection.

Therapeutic efficacy of the G1 phase arresting compounds can be determined by standard pharmaceutical procedures in cell cultures or experimental animals, e.g., for determining The $LD_{50}$ (The Dose Lethal To 50% Of The Population) and The $ED_{50}$ (the dose therapeutically effective in 50% of the population). The dose ratio between toxic and therapeutic effects is the therapeutic index and it can be expressed as the ratio $LD_{50}/ED_{50}$. Compounds, which exhibit large therapeutic indexes, are preferred. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The desired dose is preferably presented as two, three, four, five, six or more sub-doses administered at appropriate intervals throughout the day. These sub-doses may be administered in unit dosage forms, for example, containing 0.01 to 1000 mg, preferably 1 mg to 50 mg, depending on the number of sub-doses, of the G1 phase arresting compound per unit dosage form.

While it is possible for the specific G1 phase arresting compound and antiviral agent to be administered individually, either sequentially or simultaneously, it is preferable to present them together, as combined in a pharmaceutical composition.

The compositions of the present invention may comprise both the above-discussed ingredients, together with one or more acceptable carriers thereof and optionally other therapeutic agents. Each carrier must be "pharmaceutically acceptable" in the sense of being compatible with the other ingredients of the formulation and not injurious to the subject.

The present invention provides a method for the treatment or prophylaxis of a viral infection such as retroviral infections which may be treated or prevented in accordance with the invention include human retroviral infections such as human immunodeficiency virus. The specific G1 phase arresting compounds, compositions and methods according to the invention are especially useful for the treatment of AIDS and related HIV-positive conditions. The compounds of the present invention are also useful for the treatment of asymptomatic infections or diseases in humans caused by or associated with human retroviruses.

The therapeutic compositions according to the present invention may be employed in combination with other-therapeutic agents for the treatment of viral infections or conditions. Examples of such further therapeutic agents include agents that are effective for the treatment of viral infections or associated conditions such as immunomodulatory agents such as thymosin, ribonucleotide reductase inhibitors such as 2-acetylpyridine 5-[(2-chloroanilino)thiocarbonyl] thiocarbonohydrazone, interferons such as alpha-interferon, 1-beta-D-arabinofuranosyl-5-(1-propynyl)uracil, 3'-azido-3'-deoxythymidine, ribavirin and phosphonoformic acid.

Routes of Administration

The compositions according to the present invention, may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

Pharmaceutical formulations of the present invention include those suitable for oral, rectal, nasal, topical (including transdermal, buccal and sublingual), vaginal or parenteral (including subcutaneous, intramuscular, intravenous and intradermal) administration.

The formulations may conveniently be presented in unit dosage form and may be prepared by methods known in the art of pharmacy. Such methods include the step of bringing into association the G1 phase arresting compound and optionally an antiviral agent with the carrier. The carrier optionally comprises one or more accessory ingredients. In general, the formulations are prepared by uniformly and intimately bringing into association the separate ingredients with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the G1 phase arresting compound and optionally an antiviral agent such as a CCR5 antagonist: 1) in an optionally buffered, aqueous solution; or 2) dissolved and/or dispersed in an adhesive; or 3) dispersed in a polymer.

Formulations of the present invention suitable for oral administration may be presented as discrete units such as capsules, caches or tablets, each containing a predetermined amount of the ingredients; as a powder or granules; as a solution or a suspension in an aqueous or non-aqueous liquid; or as an oil-in-water liquid emulsion or a water-in-oil liquid emulsion.

A tablet may be made by compression or molding, optionally with one or more accessory ingredients. Compressed tablets may be prepared by compressing in a suitable machine the G1 phase arresting compound and antiviral agent in a free-flowing form such as a powder or granules, optionally mixed with a binder (e.g. povidone, gelatin, hydroxypropylmethyl cellulose), lubricant, inert diluent, preservatives, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of one or more of the ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising one or more of the G1 phase arresting compounds and optionally an antiviral agent in a flavored basis, usually sucrose or acacia; pastilles comprising one or more of the ingredients in an inert basis such as gelatin and glycerin, or sucrose and acacia; and mouthwashes comprising the one or more of the ingredients in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing, in addition to the one or more of the compounds of the present invention, such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

For a perinatal subject, the drug combination of the present invention may be, for example, administered orally after 36 weeks of pregnancy and continued through delivery. Interventions around the time of late gestation and delivery (when the majority of transmissions are thought to occur) are most efficacious.

In addition to the compositions described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres that offer the possibility of local noninvasive delivery of drugs over an extended period of time. The administered therapeutic is slowly released from these microspheres and taken up by surrounding tissue cells (e.g. endothelial cells).

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Suitable G1 cell cycle agents, can be used in HIV treatment strategies that allow for continued viral suppression to be maintained with less dependence on combination antiretroviral (ARV) therapy. The current goal of ARV is to obtain viral suppression as low as possible for as long as possible. Requiring less frequent dosing or a decreased quantity of ARV to control viral suppression directly addresses the problems, set forth below, associated with achieving the current goals of antiretroviral therapy including:

1. Current regimens of HAART are cumbersome and complicated and require sustained tolerance and strict adherence to 3 or more drugs.
2. Long term tight adherence may be impossible for most patients.
3. Long term tolerance to accumulating medication toxicities may be impossible for most patients.
4. Current treatment guidelines for HIV infection recommend a relatively late initiation of HAART because of the inability to eradicate the infection with HARRT alone and the risk of drug-related side-effects, including serious metabolic syndromes.
5. Some patients who have not been treated until later stages of the disease will have a high level of viral load, which could increase the risk of transmission and cause a public health problem.
6. Lastly, the vast majority of HIV infected people worldwide have no access to antiretroviral drugs due mostly to cost.

By incorporating G1 cell phase arresting agents into therapeutic approaches with the focus shifted towards maintaining long term viral control, with less complex, less toxic, and more affordable regimens, that can be applicable throughout the world. The present invention that targets the G1 cellular cycle to reduce expression of CCR5 receptors in activated T Cells cab be used successfully to maintain viral suppression in chronic HIV-1 infection without the need of continuous therapy with multiple antiretroviral drugs. These results have a positive impact on cost, side effects, and availability of HIV therapy.

The present invention is further illustrated by the following examples that should not be construed as limiting in any way.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D: Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Methods and Materials

Cell Culture and Flow Cytometry: Cultures of peripheral blood mononuclear cells (PBMCs) and monocyte-derived macrophages (MDMs) were performed on normal donors as described (Poli, 1993; Perno, 1993). PBMCs were maintained in the presence of 100 units/ml rhIL-2 (Roche Molecular Biochemicals). Cell viability was determined by Trypan blue staining or by the MTT assay (Roche Molecular Biochemicals).

RAPA was purchased from Calbiochem. The CCR5 antagonist, TAK-779 was obtained from the National Institutes of Health AIDS Research and Reference Reagent Program (Rockville, Md.).

CCR5 surface expression was measured on PBMCs cultured in the presence of IL-2 for 7-10 days. Staining was done as described (Lane, 1999) but using CCR5 mAb 182 (R & D Systems). Background staining was determined by adding an isotype-matched control (IgG2b, R&D Systems) instead of the anti-CCR5 mAb. Data were acquired by using a FACS-Calibur flow cytometer (BD Biosciences) and analyzed by using FLOWJO (Tree Star, San Carlos, Calif.).

Levels of the β-chemokines MIP-1α, MIP-1β, and RANTES were measured in culture supernatants by using ELISA kits (R & D Systems).

Infectivity Assays: The following viruses were used in infection experiments: HIV-1 IIIb, HIV-1 ADA, HIV-1 BaL, HIV-1 JRFL, HIV-1 JRCSF, and HIV-1 SF162. HIV-1 IIIb is a T cell line-adapted lab strain that uses CXCR4 for entry into cells, whereas the rest are isolates that use CCR5. Viruses were obtained from the National Institutes of Health AIDS Research and Reference Reagent Program.

For infection of PBMCs, fresh donor PBMCs were cultured for 7 days in medium containing IL-2. On day 7, cells were exposed to the virus for 3 h. Nonadsorbed virus was removed by washing cells with PBS three times. Infected cells were cultured in IL-2 medium. Infection of MDMs was carried out as described before (Perno, 1993). Unless otherwise indicated, PBMCs were infected by using an moi of 0.001, and MDM were infected by using an moi of 0.002. Virus growth was monitored in culture supernatants by measuring p24 antigen levels by ELISA (NEN) or by measuring viral RT activity in an RT assay (Willey, 1988).

PCR Methodologies: Amplification of CCR5 and β-chemokine RNA sequences was performed by RT-PCR as described (Baba, 1996; Levine, 1996). In some experiments, the effect of RAPA treatment on virus entry in PBMCs was investigated by DNA PCR. Briefly, PBMCs that had been treated with IL-2 and RAPA for 7 days were infected for 3 h with HIV-1 IIIb or HIV-1 ADA at an moi of 0.05. Virus inocula had been first filtered through a 0.22-μm filter and then treated with DNase (10 μg/ml) for 30 min at 37° C. to decontaminate the inoculum of HIV-1 DNA. Infected cells were washed extensively to remove residual virus. At 24 h after infection, cell lysates were prepared, and aliquots were amplified by DNA PCR using primer pair M661/M667 (Zack, 1990). Amplified products were detected by liquid hybridization using a $^{32}$P-labeled probe (Spina, 1995). Intensities of hybridization signals were measured in a phosphoimager. β-Actin primers were used to control for DNA amount input in the sample.

Example 1

Effect of RAPA on PBMC Proliferation and Viability: Purified PBMCs from normal donors were cultured in the presence of IL-2 and RAPA (10-fold serial dilutions, from $10^4$ to 0.01 nM). On day 7, the extent of cell proliferation was measured by the MTT assay. Representative results obtained on one of two independent experiments, each using cells from four donors, are shown. For each donor, data values are mean±SD of three independent wells. Reduced proliferation, measured by the MTT assay on day 7, was detected at drug concentrations ≧1 nM as shown in FIG. 1. Drug toxicity was observed at drug concentrations above $10^3$ nM (data not shown).

Example 2

Figure 2A:
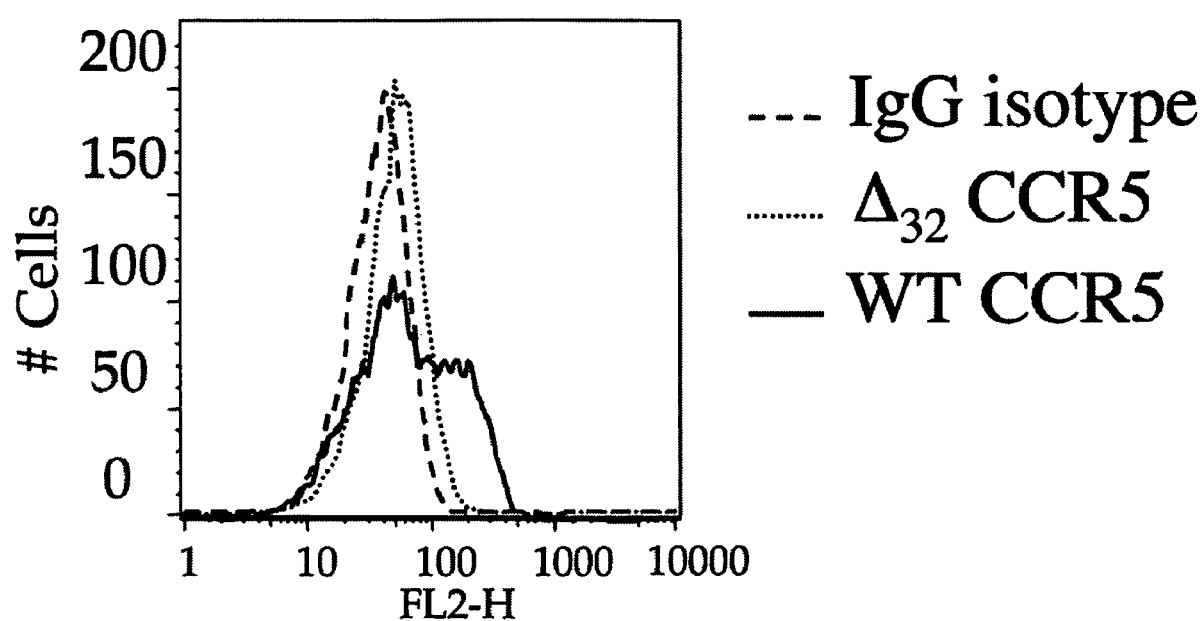
FIGS. 2A-D show the effectiveness of RAPA in down-regulating CCR5 expression on T cells and monocytes; 2A shows specific detection of CCR5 surface expression on CD4$^+$ T cells, from a normal donor, but not on CD4$^+$ T cells from an individual homozygous for the Δ32 mutation in the CCR5 gene; 2B shows down-regulation of CCR5 surface expression on CD4$^+$ T cells by RAPA in PBMCs that were cultured for 7 days in the presence of IL-2 and RAPA and then assayed for CCR5 levels, wherein expression of CCR5 on CD4$^+$ T lymphocytes is shown as a solid line, and fluorescence due to the IgG isotype control is shown as a dashed line; 2C shows inhibition of CCR5 mRNA transcription in PBMCs by RAPA. Total RNA was isolated from PBMCs that had been cultured in the presence of IL-2 and RAPA for 7 days (cells from same experiment as shown in 2B). Equivalent amounts of RNA were subjected to RT-PCR using primer pairs specific for the amplification of CCR5 mRNA (Upper) and 18S ribosomal RNA (Lower); 2D shows RAPA down-regulates CCR5 cell-surface expression on maturing monocytes that were cultured for 5 days in the presence of RPMI 20/10% ABHS and RAPA were dually immunostained for CD14 and CCR5. Changes in CCR5 surface expression were examined in CD14-gated cells. The immunofluorescence profile obtained with the anti-CCR5 mAb 182 (solid line) is compared with that of the IgG2b isotype control (dashed line). Results in 2B and 2C are representative of data obtained in PBMCs from five different donors. Results in 2D are representative of similar profiles obtained on three different donors.

RAPA Down-Regulates CCR5 Expression on T Lymphocytes and Monocytes: The specificity of the CCR5 was determined using surface-staining protocol by measuring CCR5 expression on lymphocytes from a normal donor and from a donor previously characterized as homozygous for the Δ32 mutation in the CCR5 gene. Before staining, PBMCs from both donors were cultured for 7 days in the presence of IL-2 because these culture conditions up-regulate CCR5 surface expression (Bleul, 1997). Results, depicting CCR5 expression on gated CD4 T cells, are shown in FIG. 2A. The results show specific detection of CCR5 surface expression on $CD4^+$ T cells from a normal donor, but not on $CD4^+$ T cells from an individual homozygous for the Δ32 mutation in the CCR5 gene. The results indicate that the methodology used in the present example can specifically detect CCR5 surface expression.

Figure 2B:
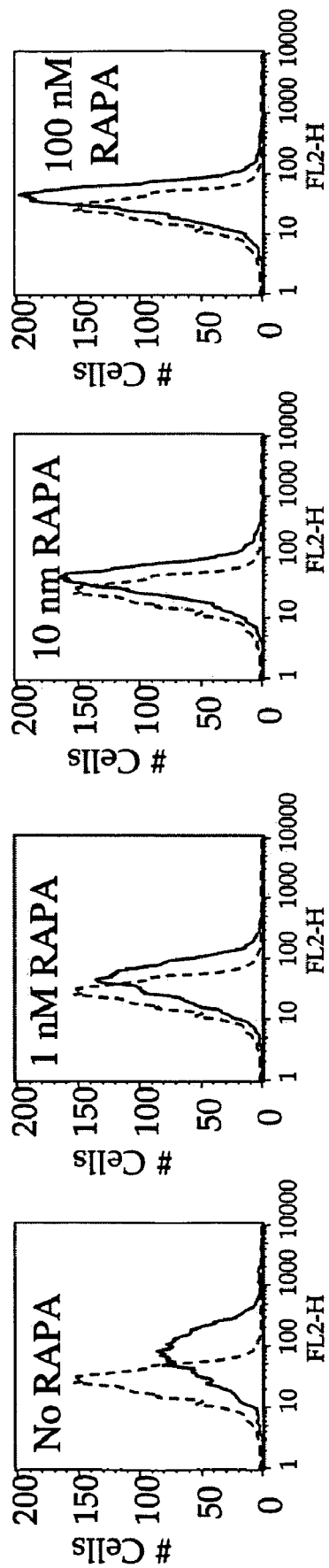

To determine the effect of RAPA on CCR5 surface expression on lymphocytes from normal donors, fresh donor PBMCs were cultured in IL-2 medium in the presence of increasing concentrations of RAPA (0.1, 1, 10, and 100 nM) for 10 days. On days 7 and 10, CCR5 surface expression on CD4 and CD8 T lymphocytes was measured by dual staining with anti-CD4 and anti-CD8 antibodies in combination with anti-CCR5 mAb 182 and analysis on the FACS. Day 7 and 10 results indicated that RAPA concentrations ≧1 nM down-regulated CCR5 surface expression on CD4 lymphocytes in the five donors tested. RAPA at 0.1 nM down-regulated CCR5 protein expression on CD4 lymphocytes from some but not all donors. Representative day 7 results, showing concentrations of RAPA that effectively down-regulated CCR5 in all donors, are depicted in FIG. 2B. A similar decrease on CCR5 expression was evident on the CD8 lymphocyte subset, and CCR5 down-regulation in both CD4 and CD8 lymphocyte subsets was also observed on day 10 (data not shown).

Figure 2C:
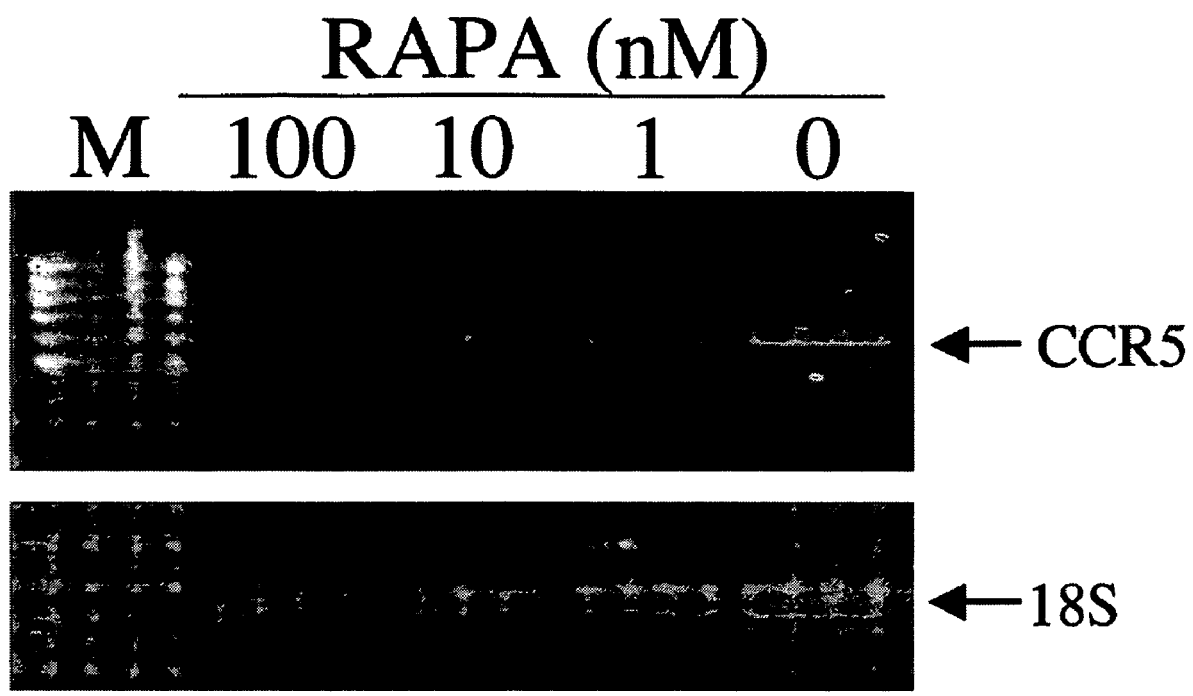

At the transcription level, semiquantitative RT-PCR analysis of RNA isolated from RAPA-treated PBMC cultures showed decreased amounts of CCR5 transcripts in the presence of drug (FIG. 2C Upper). RT-PCR analysis of ribosomal 18S RNA indicated similar RNA content among samples yielding reduced levels of CCR5 transcripts (FIG. 2C Lower). In addition, amplification of RNA samples in the absence of the RT step gave no amplification signal, thus ruling out the possibility of cellular DNA contamination in the RNA preparations (data not shown).

Figure 2D:
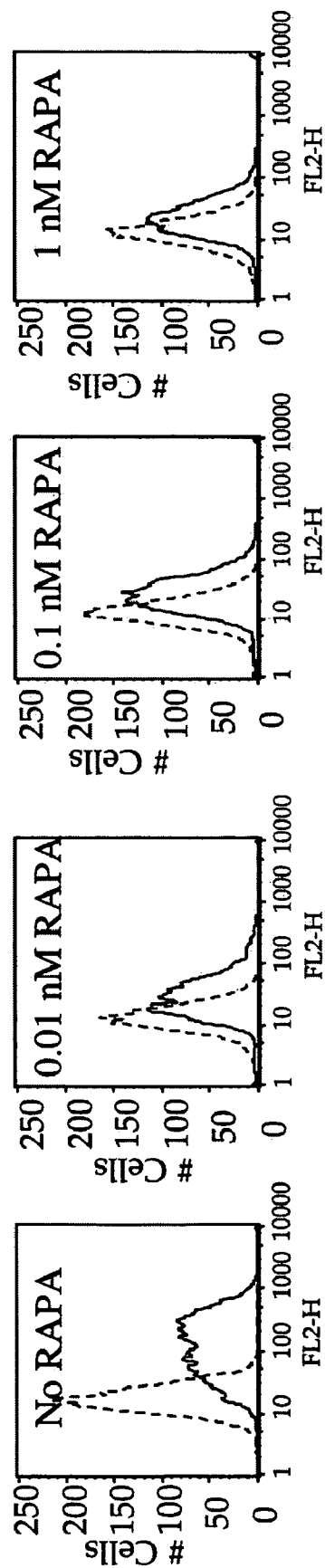

Similarly, RAPA down-regulates CCR5 cell-surface expression on maturing monocytes. Monocytes cultured for 5 days in the presence of RPMI 20/10% ABHS and RAPA were dually immunostained for CD14 and CCR5. Changes in CCR5 surface expression were examined in CD14-gated cells. The immunofluorescence profile obtained with the anti-CCR5 mAb 182 (solid line) is compared with that of the IgG2b isotype control (dashed line), as shown in FIG. 2D. Monocytes cultured for 5 days in the presence of RAPA showed reduced levels of CCR5 surface expression as compared with the drug-untreated cultures. Experiments using monocytes from three different donors showed consistent down-regulation of CCR5 surface expression at RAPA concentrations as low as 0.01 nM. These results show that RAPA reduces CCR5 surface expression on cultured T lymphocytes (both CD4 and CD8) and monocytes. Together with the RT-PCR results in PBMCs, these results indicate that RAPA interferes with CCR5 expression by reducing gene transcription.

Example 3

Figure 3A:
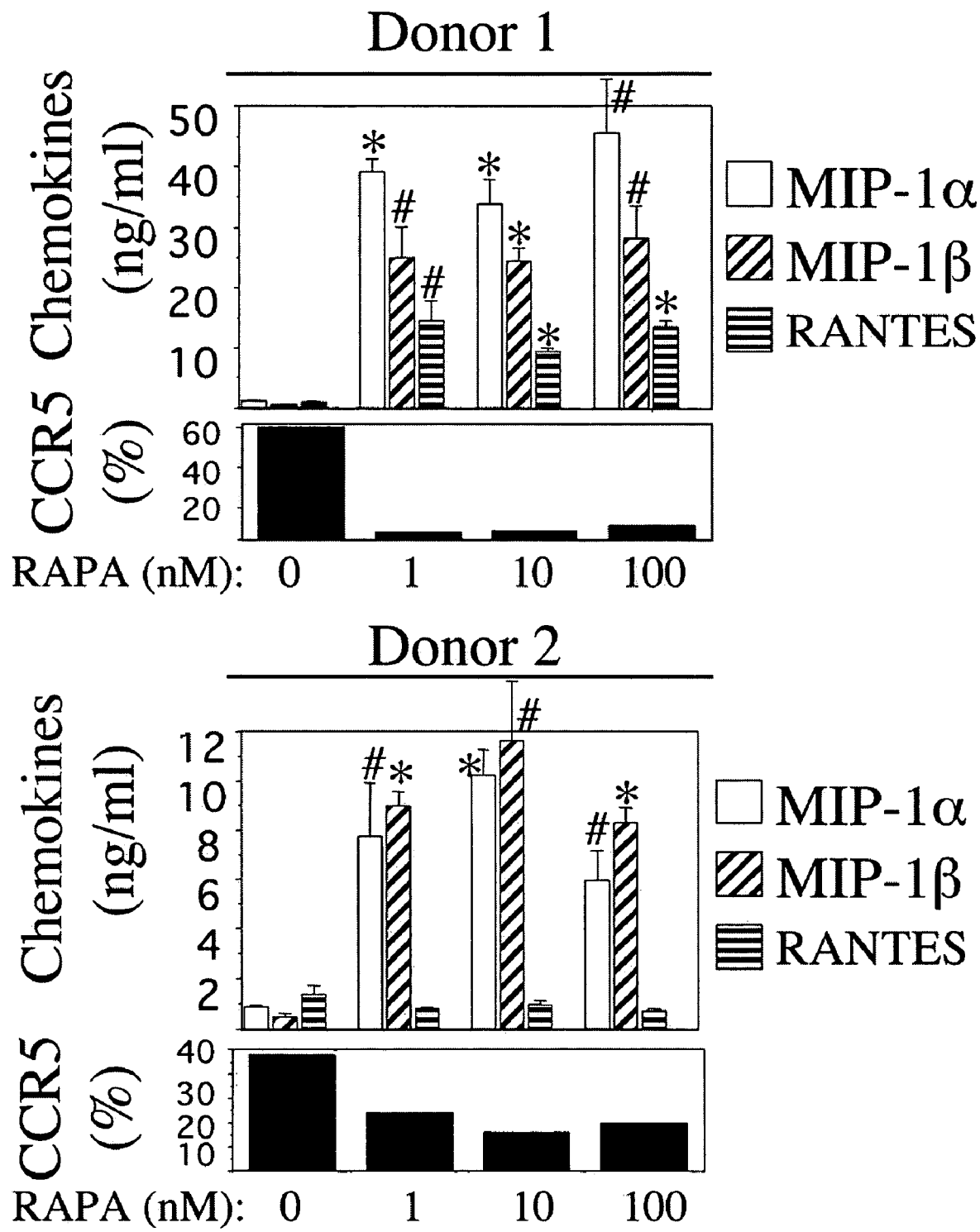
FIGS. 3A and 3B shows that RAPA increases extracellular β-chemokine levels in PBMC cultures. 3A shows the results of donor PBMCs that were cultured in the presence of IL-2 and RAPA for 10 days, at which time supernatants were evaluated for β-chemokine content by ELISA and cells were stained for CCR5 expression. Percentage of CD4 lymphocytes expressing CCR5 at each concentration of RAPA is indicated. Results shown in two donors are representative of four experiments using four different donors. *, $P<0.01$; #, $P<0.05$, compared with untreated control by Student's t test; 3B shows the effect of RAPA on extracellular levels of MIP-1β in cultures of CCR5-null PBMCs. Levels of MIP-1β protein in the presence and absence of RAPA were measured in supernatants of IL-2-stimulated PBMCs from a normal donor and from a donor homozygous for the Δ32 mutation in the CCR5 gene. Values were obtained on day 10 of culture and are means±SD of duplicate wells.

RAPA Increases Extracellular Levels of MIP-1α and MIP-1β in PBMC Cultures: Because lymphocytes and monocytes cultured in the presence of RAPA presented reduced CCR5 RNA and protein levels, the levels of the CCR5 ligands MIP-1α, MIP-1β, and RANTES were measured in supernatants of RAPA-treated PBMC cultures. PBMCs from four donors were cultured in the presence of IL-2 and RAPA for 10 days. On day 10, percentage of cells expressing CCR5 and supernatant chemokine content were determined for each donor. As in previous experiments, RAPA treatment resulted in reduced levels of CCR5 protein expression. When chemokine content in culture supernatants was measured, it was found that MIP-1α and MIP-1β levels were higher in the presence of RAPA than in its absence in all four donors. Among the different donors, RAPA-treated cultures contained 6-39-fold higher levels of MIP-1α than untreated cultures. Similarly, MIP-1β levels were increased 17-47-fold in the presence of RAPA as compared with untreated controls. In contrast, levels of RANTES in the presence of RAPA were increased in two donors while remaining unchanged or even decreasing in the others. Chemokine results obtained in two of the donors, showing disparity of RANTES levels in the presence of RAPA, are depicted in FIG. 3A.

To determine whether the increased levels of MIP-1α and MIP-1β proteins detected in the supernatants of RAPA-treated cells were the result of increased transcriptional activity, total RNA from RAPA-treated and untreated cultures was amplified by semiquantitative RT-PCR. Amplification of RNA isolated in days 3, 7, and 10 of culture with primer pairs specific for MIP-1α and MIP-1β showed no differences in transcript amount for either chemokine between RAPA-treated and untreated cultures (data not shown). These data suggested that RAPA does not augment extracellular MIP-1α/β levels by enhancing the production of chemokine transcripts.

Figure 3B:
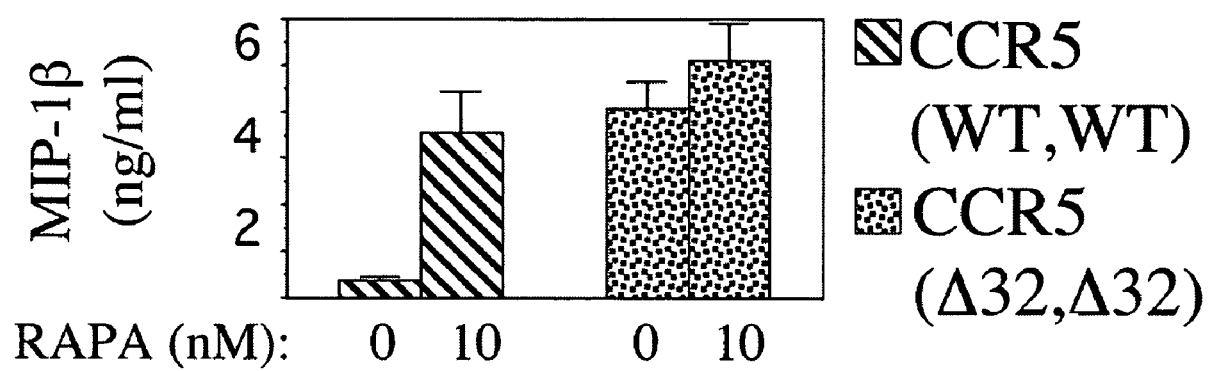

The above results, showing that RAPA treatment of cells resulted in reduced amounts of CCR5 transcripts (and protein levels) without enhancing the production of chemokine transcripts, suggested that the observed increases on MIP-1α/β proteins is due to a lack of chemokine uptake on RAPA-treated cells. The above results were confirmed by evaluating the effect of RAPA on the secretion of MIP-1β, a chemokine that uses CCR5 as its only receptor, in cultures of PBMCs derived from a donor homozygous for the Δ32 mutation in the CCR5 gene. In this experimental setting, in which MIP-1β cannot be endocytosed by CCR5, the effect of RAPA on MIP-1β protein levels provided information regarding the mechanism by which RAPA increases β-chemokine levels. To this end, stimulated PBMCs from two normal donors and from a CCR5-null donor were cultured in the presence of RAPA as in previous experiments. MIP-1β levels in supernatants were evaluated on day 10. Representative results obtained in one of the normal donors are shown in FIG. 3B next to the results obtained on the CCR5-null donor. In the normal donor, RAPA treatment resulted in an increased level of MIP-1β protein (9.3-fold increase as compared with the RAPA-untreated control) as expected from previous experiments. However, MIP-1β levels in the CCR5-null donor were only increased by 1.2-fold in the presence of RAPA. Together, these results show that increased levels of MIP-1β protein, and additionally MIP-1α, in the presence of RAPA reflect chemokine accumulation due to diminished uptake by cells presenting reduced levels of CCR5 co-receptor.

Example 4

Figure 4A:
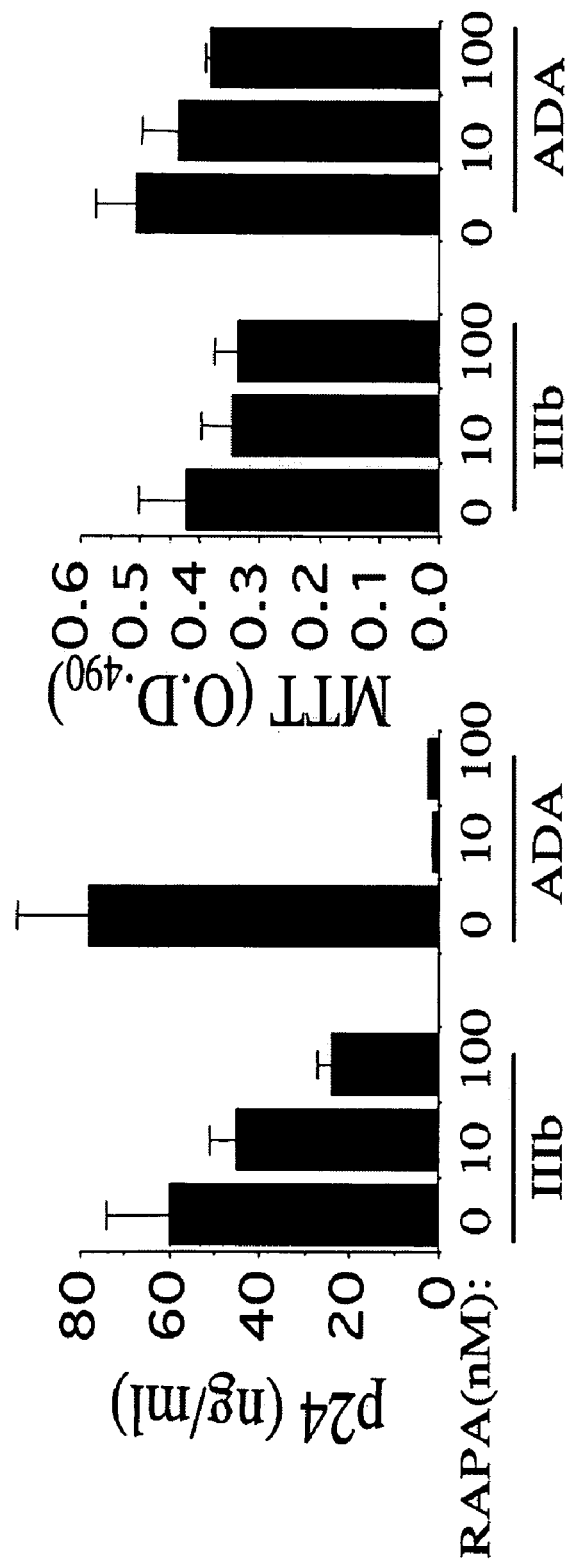
FIGS. 4A-4C show RAPA inhibition of HIV-1 replication in PBMCs, and that the antiviral activity in R5 HIV-1 is greater than in X4 HIV-1. 4A shows the results of a replication in seven-day testing period wherein RAPA-treated PBMCs were infected with HIV-1 IIIb or HIV-1 ADA. Infected cells were cultured in the presence of drug RAPA for 7 days, at which time virus replication was measured by p24 and cell viability was measured by the MTT assay. Results (means ±SD of triplicate wells) are representative of seven independent experiments, each on cells from a different donor; 4B shows effects on HIV-1 IIIb and HIV-1 ADA infected DNase-treated stock of PBMCs when treated with or without 100 nM RAPA. HIV-1 DNA sequences were amplified by PCR in cellular lysates prepared 24 h after infection. Amplified PCR products were detected with a radioactive probe. "+" indicates presence of RAPA in the PBMC culture before and after infection; "-" indicates no RAPA treatment. Amplification of β-actin sequences indicated same amount of cellular DNA among the different cell lysates (data not shown). NC denotes PCR negative control; 4C shows the antiviral activity of low concentrations of RAPA when investigated in a panel of R5 strains of HIV-1. Cell proliferation was assayed on uninfected cells from same donor cultured under identical conditions. Results (means ±SD of triplicate wells) are representative of three independent experiments, each on different donor cells.

Antiviral Activity of RAPA in PBMCs: The antiviral activity of RAPA was assayed in PBMCs that had been cultured in the presence of RAPA for 7 days before infection. Cells were infected with the X4 HIV-1 IIIb and the R5 HIV-1 ADA strains. Infected cells were cultured in the presence of RAPA (same concentration as during pretreatment) for 7 additional days, during which time virus replication and cell viability were measured. In a total of seven different experiments using cells from different donors, the antiviral effect of RAPA was more potent against HIV-1 ADA than against HIV-1 IIIb. The results shown in FIG. 4A for one donor, show that at 10 nM RAPA, the average value of HIV-1 ADA inhibition in the seven experiments was 91% (range of 88-97%), whereas at 100 nM RAPA, HIV-1 ADA was inhibited by 94% (range of 92-99%). In contrast, 10 nM RAPA inhibited HIV-1 IIIb by 13.5% (range of 5-25%), and 100 nM RAPA inhibited HIV-1 IIIb by 32% (range 29-60%).

Figure 4B:
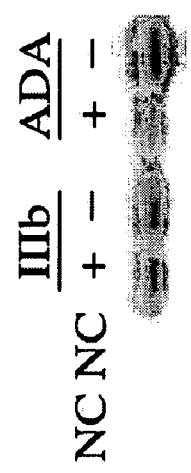

To further demonstrate the disproportionate antiviral effect of RAPA on R5 versus X4 HIV-1 strains, the antiviral effect of the drug was next assessed by measuring viral DNA in cells shortly after infection. Donor PBMCs that had been cultured for 1 week in the presence (100 nM RAPA) or absence of drug were infected with DNase-treated stocks of R5 HIV-1 ADA or X4 HIV-1 IIIb. At 24 h after infection, cell lysates were prepared and amplified for HIV-1 DNA sequences by PCR. Amplified PCR products were detected by using a radiolabeled probe. As shown in FIG. 4B, phosphoimager analyses of the radioactive signals indicated that HIV-1 IIIb DNA content was the same in the RAPA-treated and untreated cells. In contrast, HIV-1 ADA DNA content in the RAPA-treated cells was three times lower than in the untreated cells. Primer pairs specific for the β-actin gene indicated the same DNA input among samples (data not shown).

Figure 4C:
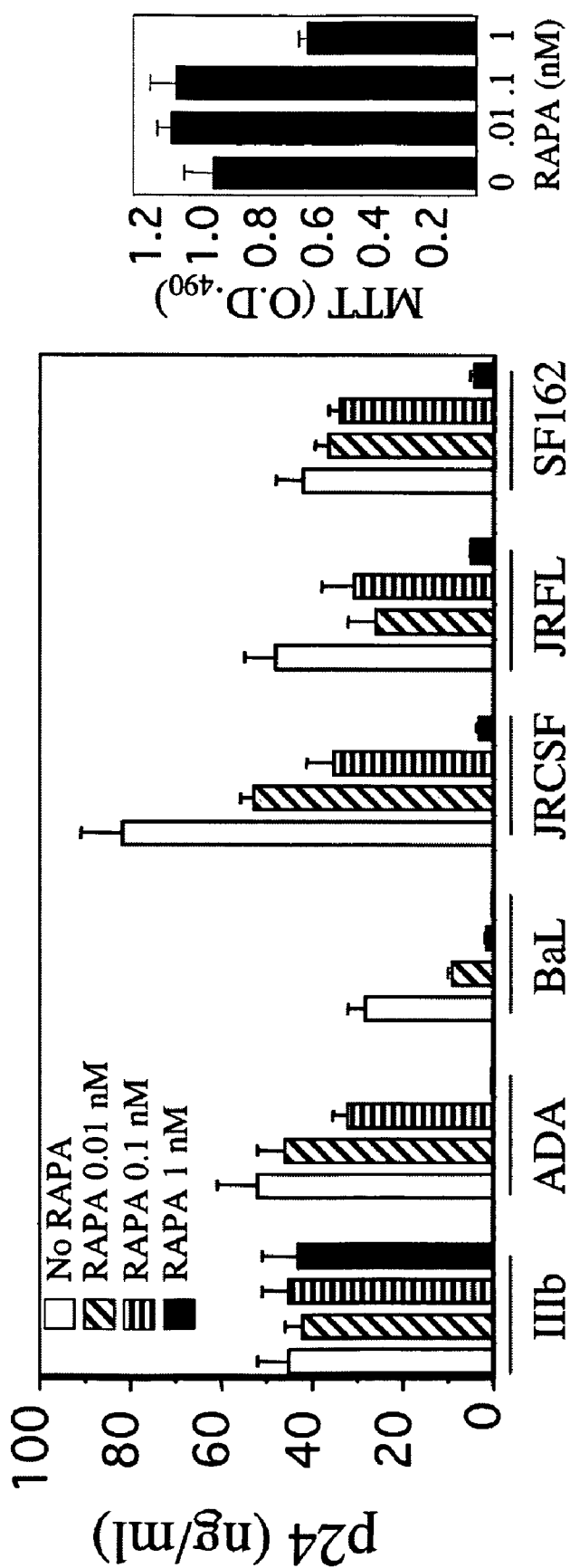

As the results obtained with HIV-1 IIIb and HIV-1 ADA suggested that RAPA exerted a more potent antiviral effect in R5 than in X4 HIV-1, the antiviral activities of low concentrations of RAPA (0.01, 0.1, and 1 nM) were next evaluated against a panel of five R5 strains of HIV-1, with the results shown in FIG. 4C. At these concentrations of RAPA, antiviral activity was seen against R5 strains but not against HIV-1 IIIb. RAPA at 0.01 nM inhibited R5 HIV-1 by 10-64% depending on the strains, whereas 0.1 nM RAPA inhibited virus replication by 15-85%. At 1 nM RAPA, all R5 viruses were inhibited by ≧90%. Together, these results demonstrate that RAPA decreases the susceptibility of PBMCs to be infected by CCR5-using strains of HIV-1 while having little effect in CXCR4-using strains.

Example 5

Figure 5:
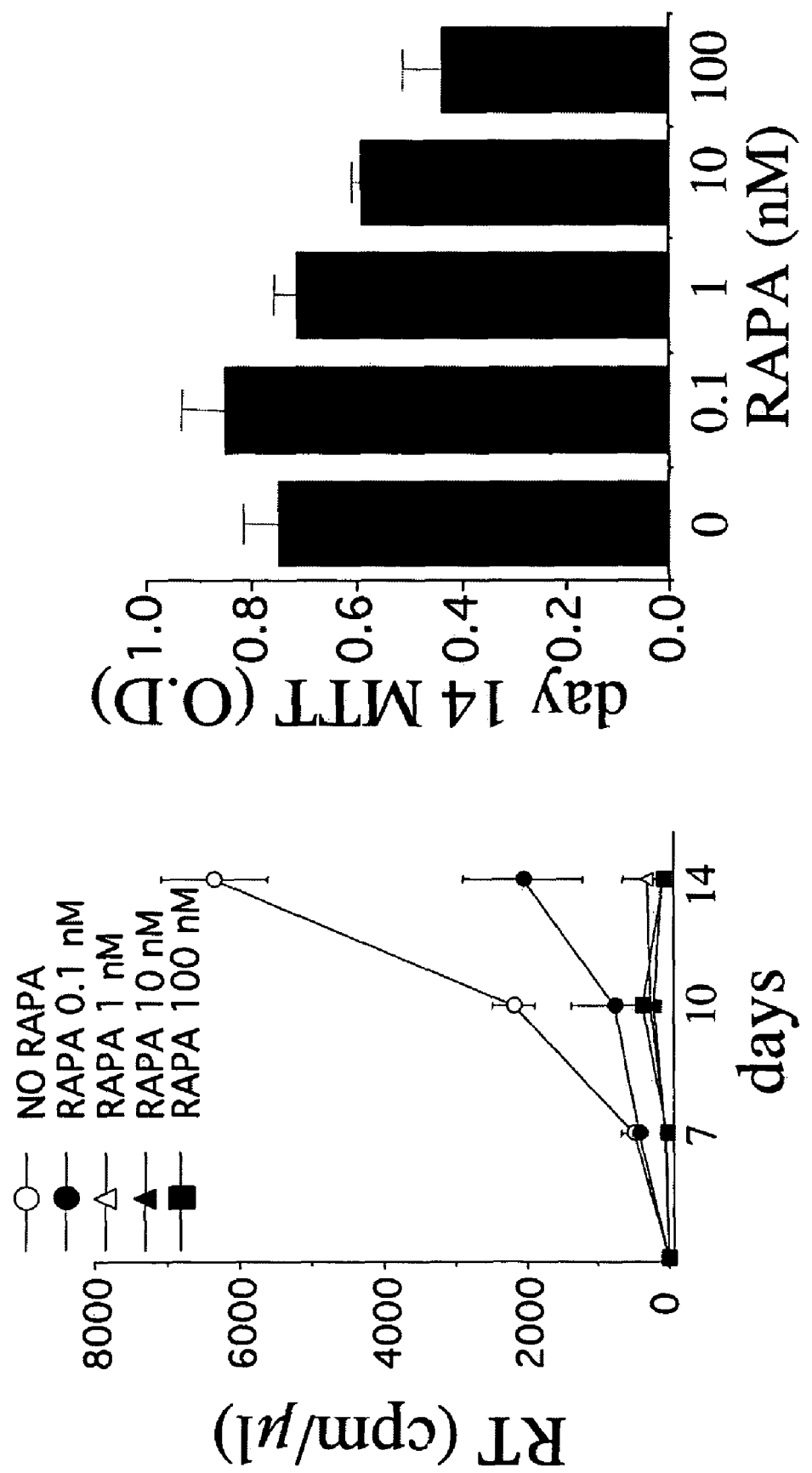
FIG. 5 shows that RAPA inhibits HIV-1 replication in MDMs. Purified monocytes were cultured for 5 days in the presence of RAPA. On day 5, cells were infected with HIV-1 ADA and cultured in the presence of RAPA for 14 additional days. On days 7, 10, and 14 after infection, virus growth was measured by the RT assay. On day 14, cell viability was determined by MTT. Results (means±SD) are representative of data obtained in three independent experiments, each using cells from a different donor.

Antiviral Activity of RAPA in Macrophages: The antiviral activity of RAPA in MDMs was first assayed under the culture conditions shown to down-regulate expression of CCR5 (see above results). To this end, donor monocytes were cultured for 5 days in the presence of RAPA. On day 5, cells were infected with HIV-1 ADA. Infected cells were cultured in the presence of RAPA for an additional 14 days. Virus production was measured on the culture supernatants on days 7, 10, and 14 after infection. Cell viability was measured by the MTT assay at the end of the experiment. Over the course of the experiment, RAPA inhibited virus replication in a dose-dependent manner. On day 14, RAPA concentrations ranging 0.1-100 nM inhibited virus production by 70-95%, as shown in FIG. 5. Cell viability at the end of experiment was reduced at RAPA concentrations ≧10 nM. In an additional experiment in which RAPA was used at 0.01 nM, the R5 viruses HIV-1 ADA and HIV-1 SF 162 were inhibited by 64% and 45%, respectively (data not shown).

In the above-described experiment, monocytes had been pretreated with RAPA during the 5-day differentiation period. To control for the possible interference of RAPA with the process of monocyte differentiation, a new infection experiment in which RAPA was not present during the 5-day monocyte differentiation period was designed. To this end, fresh monocytes were cultured for 5 days in the absence of RAPA. On day 5, cells were infected with HIV-1 ADA and then exposed to RAPA. Under these experimental conditions, two independent experiments using monocytes from two different donors indicated that 1 nM RAPA inhibited virus replication by ~60% in one of the donors and by ~80% in the other donors (virus production measured on day 14 after infection; data not shown).

Taken together, these results show that RAPA treatment of differentiating monocytes interferes with their ability to become susceptible targets for HIV infection and that RAPA also interferes with the ability of HIV to replicate in already differentiated macrophages.

Example 6

Figure 6:
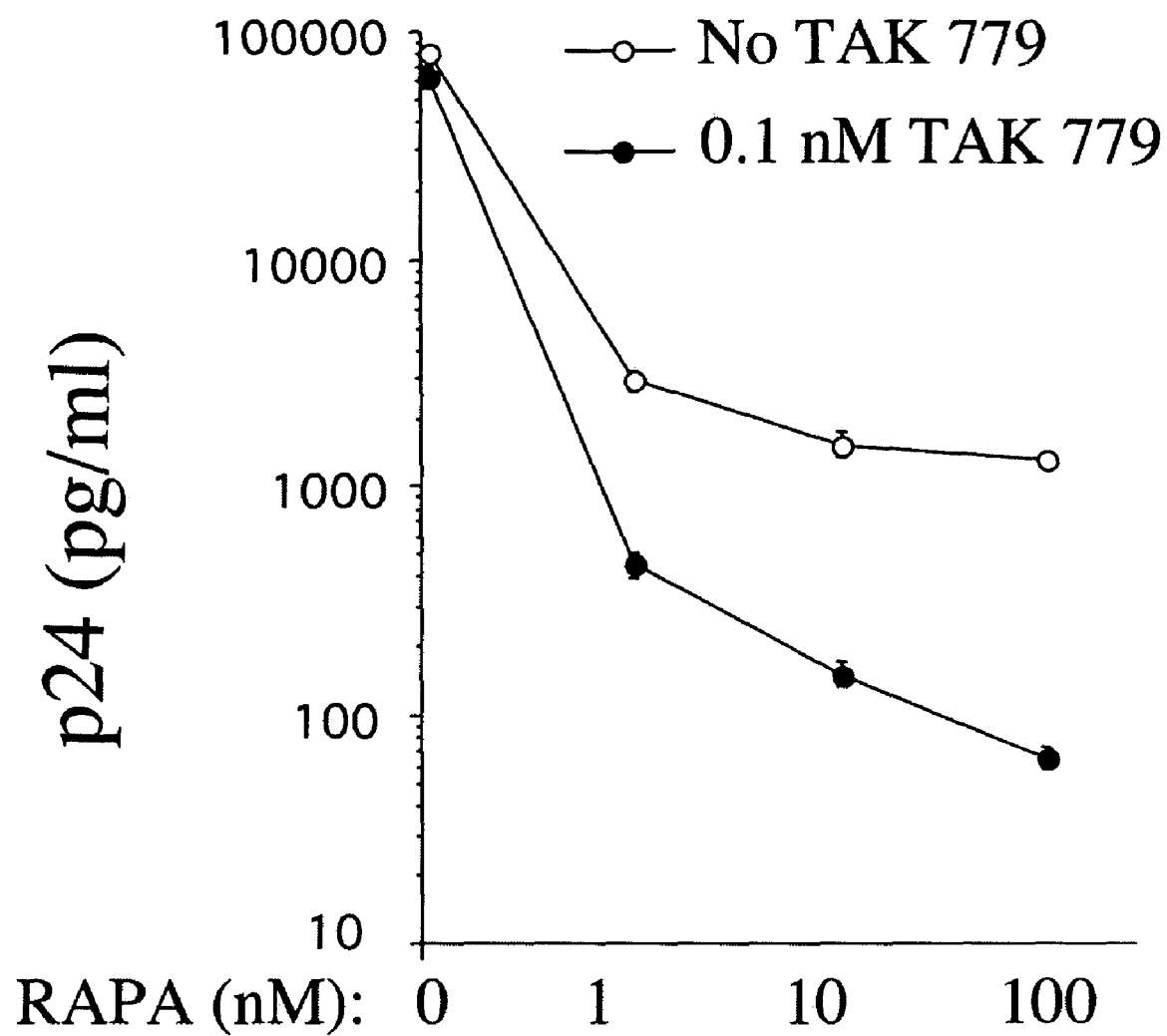
FIG. 6 shows that RAPA enhances the antiviral activity of the CCR5 antagonist TAK-779. PBMCs that had been cultured in the absence or presence of RAPA (1, 10, and 100 nM) for 7 days were infected with HIV-1 ADA in the presence of 0.1 nM TAK-779. Infected cells were cultured in the presence of RAPA and 0.1 nM TAK-779. On day 7 after infection, virus production was measured by the p24 assay in the culture supernatant. Note the logarithmic scale in the y axis. Data represent means±SD of triplicate wells. Representative results obtained in one of three independent experiments are shown.

RAPA Enhances the Antiviral Activity of the CCR5 Antagonist TAK-779: Testing was conducted to determine whether the down-regulation of CCR5 surface expression observed in the presence of RAPA would increase the potency of a CCR5 antagonist drug. To test this hypothesis, donor PBMCs were cultured in IL-2 medium in the absence or presence of RAPA (1, 10, and 100 nM). After 7 days, cells were infected with HIV-1 ADA in the presence of 0.1 nM TAK-779, a concentration of the drug TAK-779 showing little antiviral activity. Infected cells were cultured in the presence of RAPA (same concentration as during pretreatment) plus 0.1 nM TAK-779. Virus production was determined 7 days after infection. The results as set forth in FIG. 6 show that in the absence of RAPA, 0.1 nM TAK-779 caused a 21% inhibition of virus replication. However, in the presence of 1 nM RAPA, the antiviral effect due to TAK-779 increased from 21% to 74.5% virus inhibition. Similarly, the antiviral activity of TAK-779 was increased to 89% and 96% virus inhibition in the presence of 10 and 100 nM RAPA, respectively. The TAK-779 concentration used did not affect cell viability (data not shown). These results suggest that the antiviral properties of a CCR5 antagonist drug are enhanced by RAPA.

The results shown in FIG. 6 illustrate synergic efficacy with the combination of RAPA and TAK 779. As stated above, 0.1 nM TAK-779 shows little antiviral activity and the results shown in FIG. 4 indicate that administering RAPA alone reduces the level of P24 to nanograms/ml amounts. However, the combination of both compounds reduces the levels of p24 to picograms/ml. Thus, the combination provides for a synergic reduction in replication of HIV-1.

Example 7

Figure 7:
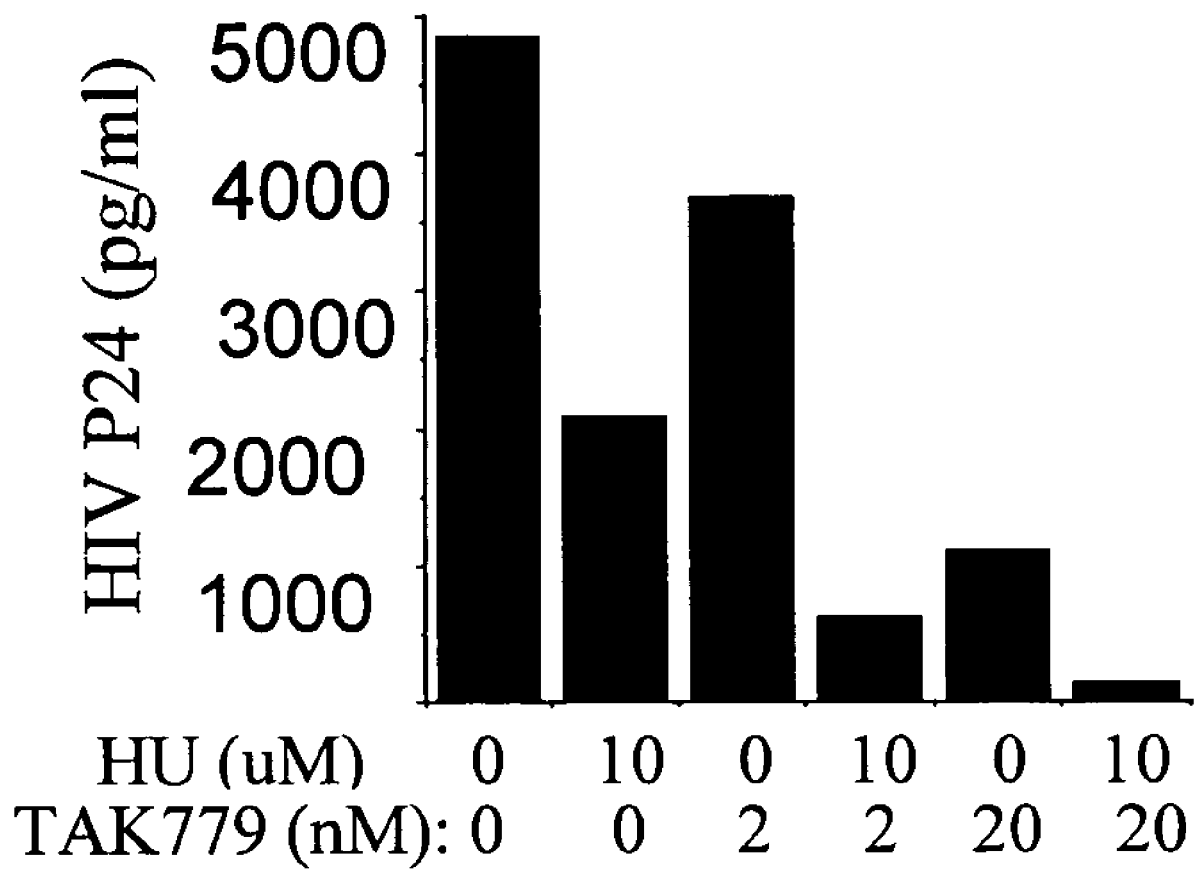
FIG. 7 shows that HU enhances the antiviral activity of the CCR5 antagonist TAK-779. PBMCs that had been cultured in the absence or presence of HU for 7 days were infected with HIV-1 ADA in the presence or absence of TAK-779. On day 7 after infection, virus production was measured by the p24 assay in the culture supernatant.

The synergic activity of RAPA and TAK-779 in reducing replication of HIV-1 is further shown with the combination of HU and TAK-779. FIG. 7 illustrates that HU synergistically enhances the antiviral activity of the CCR5 antagonist TAK-779. Donor PBMCs were cultured in IL-2 medium in the absence or presence of HU (0 and 10 uM). After 7 days, cells were infected with HIV-1 ADA. Infected cells were cultured in the presence of HU (same concentration as during pretreatment) plus different concentration of TAK-779 ranging from 0, 2 and 20 nM). Virus production was determined 7 days after infection. Combinations of TAK-779 and HU showed that without HU and TAK-799 the p24 value was approximately 5000 picograms/ml. The introduction of 10 uM of HU reduced the levels of p24 approximately 60%. The introduction of 2 nM of TAK-779 reduced the levels of p24 about 20%. However, the combination of 10 uM of HU and 2 nM of TAK-779 caused a overall reduction of approximately 90% of p24, thus indicating that the combination caused a synergic reduction in p24 levels and increased the activity of the CCR5 antagonist TAK-779. Thus, these results show a synergic increase in the activity of CCR5 antagonist.

Example 8

Figure 8A:
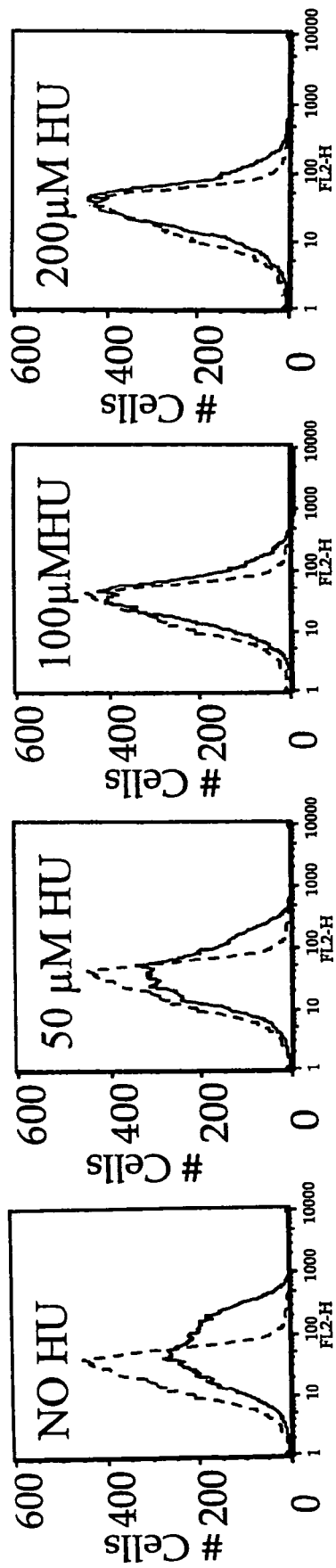
FIGS. 8A-B show the effectiveness of HU in down-regulating CCR5 expression on T cells and monocytes; 8A shows down-regulation of CCR5 surface expression on CD4+ T cells by HU in PBMCs that were cultured for 7 days in the presence of IL-2 and HU and then assayed for CCR5 levels, wherein expression of CCR5 on CD4+ T lymphocytes is shown as a solid line, and fluorescence due to the IgG isotype control is shown as a dashed line; 8B shows inhibition of CCR5 mRNA transcription in PBMCs by HU. Total RNA was isolated from PBMCs that had been cultured in the presence of IL-2 and HU for 7 days (cells from same experiment as shown in 8A). Equivalent amounts of RNA were subjected to RT-PCR using primer pairs specific for the amplification of CCR5 mRNA (Upper) and 18S ribosomal RNA (Lower)
Figure 8B:

To determine the effect of HU on CCR5 surface expression on lymphocytes from normal donors, fresh donor PBMCs were cultured in IL-2 medium in the presence of increasing concentrations of HU (0, 50, 100 and 200 uM) for 10 days. On days 7 and 10, CCR5 surface expression on CD4 and CD8 T lymphocytes was measured by dual staining with anti-CD4 and anti-CD8 antibodies in combination with anti-CCR5 mAb 182 and analysis on the FACS. Day 7 and 10 results indicated that HU concentrations ≧50 uM down-regulated CCR5 surface expression on CD4 lymphocytes in the five donors tested. At the transcription level, semiquantitative RT-PCR analysis of RNA isolated from HU-treated PBMC cultures showed decreased amounts of CCR5 transcripts in the presence of drug (FIG. 8B Upper). RT-PCR analysis of ribosomal 18S RNA indicated similar RNA content among samples yielding reduced levels of CCR5 transcripts (FIG. 8B Lower).

Example 9

In vivo effects of Rapamycin on expression of the Chemokine receptor 5 (CCR5) and accumulation of chemokines MIP 1α, MIP-1β and RANTES due to diminished uptake by cells presenting reduced expression levels of CCR5 co-receptor in volunteers with chronic HIV infection HIV-1 has been shown in most instances to use the chemokine receptor, CCR5, as a co-receptor for entry into macrophages and CD4 lymphocytes. The natural ligands for the CCR5 co-receptor are proteins called β-Chemokines. In the in vitro models, discussed above, it was demonstrated that Rapamycin, as well as other G1 cell cycle agents including hydroxyurea markedly decreased expression of CCR5 surface receptors as shown in FIGS. 2 B-C and 8 A-B.

To assess the expression activity of CCR5 and its effects on levels of CCR5 receptors in vivo, an open-labeled, non-randomized proof of concept trial was performed in which 8 volunteers with established HIV infection were given 2 mg/day of Rapamycin, following a 6 mg loading dose, for 28 days. Peripheral blood for determining expression levels of CCR5 was obtained at the screening visit, days 7, 14 and 28 of the Rapamycin dosing, and at day 42 (which was two weeks following the last dose of Rapamycin). Eight subjects were enrolled in the study and to date 3 volunteers have completed the study and Rapamycin was well-tolerated.

Figure 9:
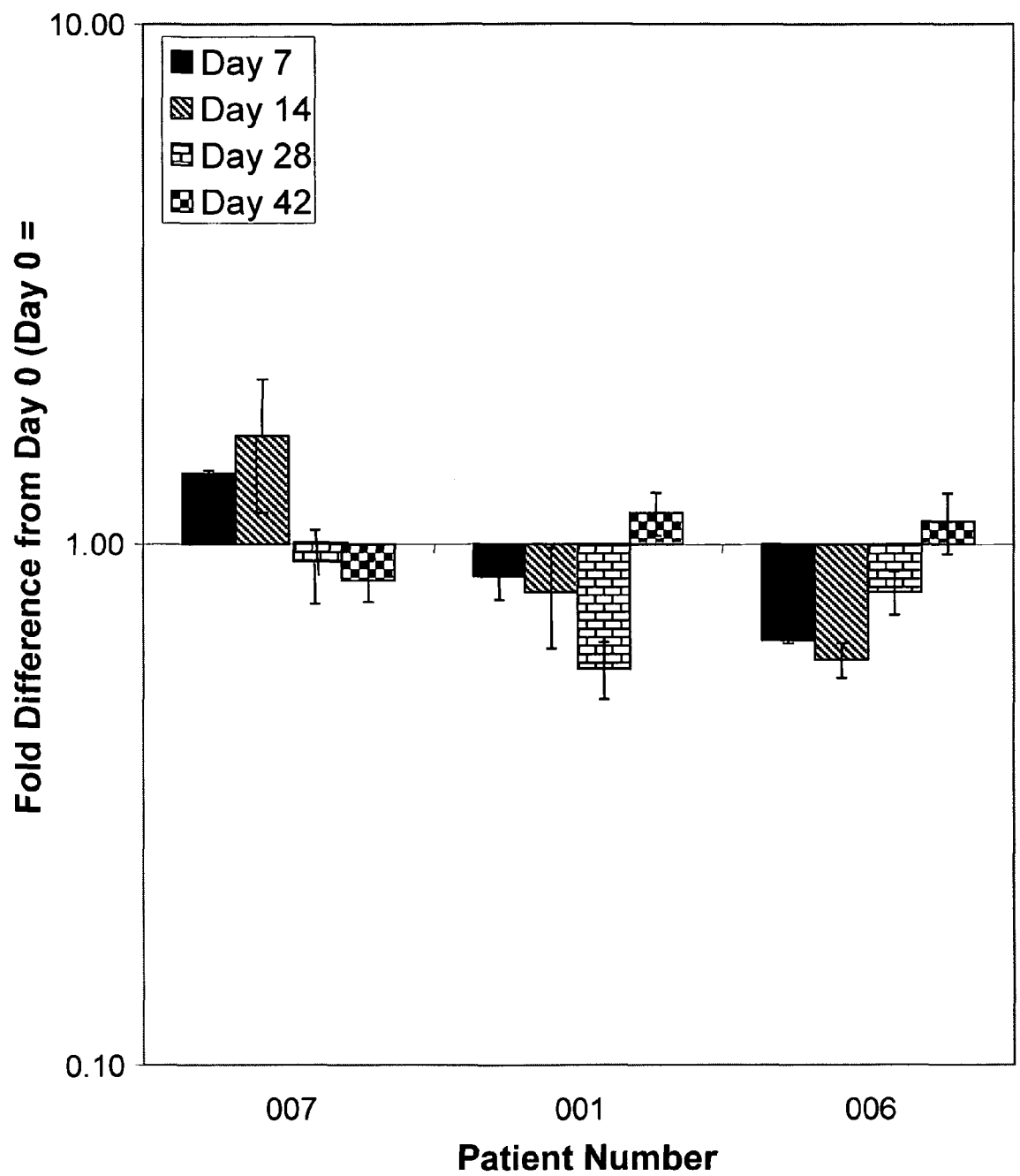
FIG. 9 shows changes from baseline of CCR5 m RNA as a measurement of CCR5 expression. Values are normalized for cell house keeping gene beta actin. Fold differences from baseline (Day 0) are noted on log scale. Timepoint tested include day 7, 14 and 28 on RAPA and then day 42, 2 weeks post discontinuation of RAPA.

FIG. 9 depicts alteration in CCR5 expression observed in HIV infected volunteers during this trial. All three volunteers demonstrated a decrease in CCR5 expression by the latest day 28 which was associated with use of RAPA. Clearly, volunteer 001 and 006 experienced an almost immediate reduction in CCR5 expression, while volunteer 007 experienced a reduction later in the treatment. Thus, altering the cell-cycle of peripheral blood mononuclear cells with a G1-specific agent, Rapamycin, resulted in the decreased RNA expression of CCR5 in HIV infected volunteers with established UV infection; and, this agent was well-tolerated.

The targeting by RAPA of a cellular component such as CCR5, as opposed to targeting of the virus itself, offers an antiviral strategy that is less likely to lead to virus resistance, as cellular components are not expected to mutate under drug pressure. The in vitro studies suggest that RAPA would be more effective in controlling the replication of R5 than X4 strains of HIV-1. In this regard, the therapeutic use of RAPA as a treatment of early HIV-1 disease (before appearance of X4 strains) is of great value, particularly in light of current guidelines that advocate delayed initiation of antiretroviral therapy (Dybul, 2002). Furthermore, the antiviral properties of RAPA are especially relevant in geographical areas where subtype C HIV-1 is present, as these viruses use CCR5 as major co-receptor (Bjornal, 1999). Subtype C HIV-1 infections have risen in prevalence over the last decade, and they currently constitute the predominant subtype worldwide (Essex, M. (1999).

Moreover, the antiviral properties of RAPA provide new treatment opportunities for suppression of allograft rejection in HIV-infected subjects undergoing solid organ transplantation. The antiviral properties of RAPA, coupled with its anti-angiogenic properties (Guba, 2002), suggest that RAPA offers a better choice for HIV patients undergoing organ transplantation.

In summary, the ability of RAPA to down-regulate CCR5 co-receptor expression and to augment extracellular levels of β-chemokines offers a new strategy with important implications for the treatment and prevention of HIV-1 infection. The combination of RAPA and CCR5 antagonists is especially effective in controlling virus replication in patients.

Example 10

Figure 10:
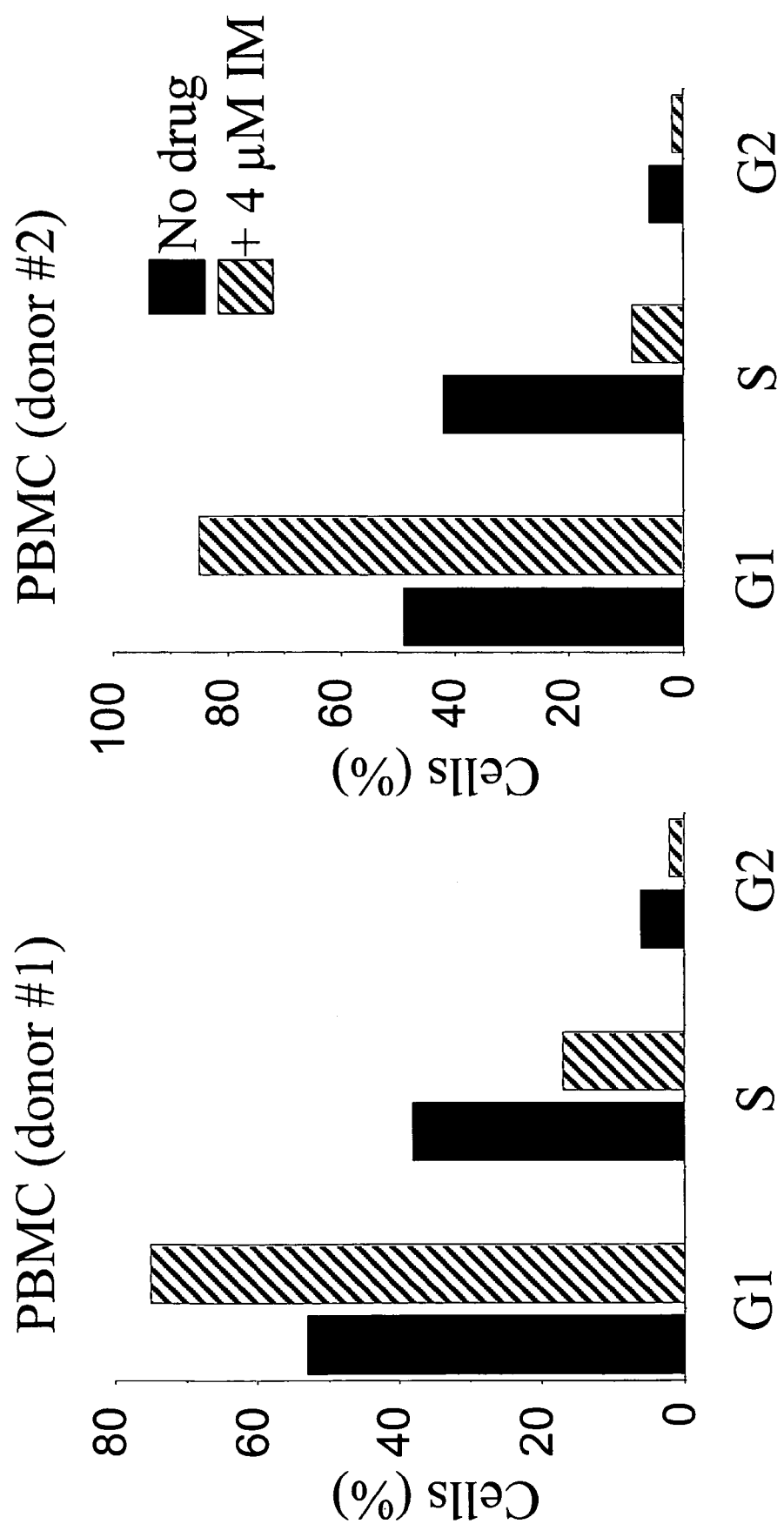
FIG. 10 shows the results of the use of Indirubin-3'-moxime (IM) as a G1 phase arresting agent and the percentages of cells in each phase of the cell cycle.

Indirubin-3'-monoxime (IM) arrests human lymphocytes in G1 phase. PBMCs from 2 normal donors were activated in absence and presence of 4 µM Indirubin-3'-momoxime (IM) for 24 hours. Cells were then fixed with 70% Ethanol, stained with Propidium Iodide, and analyzed by Flow cytometry. Percentages of cells in each phase of the cell cycle are shown. In the presence of IM, the % of cells in G1 increases and this cycle arrest leads to lower pecentages of cells in S and G2 phases as compared to the untreated control as shown in FIG. 10.

Example 11

Rapamycin enhances the antiviral activity of T20 against R5 HIV-1. Upon binding of gp120 to CD4 and a cellular coreceptor (usually CCR5 or CXCR4), conformational changes occur in both the gp120 and gp 41 subunits. Within gp 41, the fusion peptide region becomes exposed and inserts into the cell membrane. Additional conformational changes result in the formation of a trimeric antiparallel coiled-coil structure between the HR-1 and HR-2 regions of gp 41. The formation of the six helix bundle is believed to bring the viral and cell membranes together and lead to viral entry.

T20 acts by binding to the HR-1 region of gp 41 thereby preventing the interaction between the HR-1 and HR-2 domains of gp 41 that is required for virus/host membrane fusion. Several factors (host and viral) have been identified as influencing the fusion kinetics, and therefore having an impact on T20 sensitivity. Among the host factors, the rate of virus-cell fusion is dependent on the level of CCR5 expression on the cell surface, with higher levels of coreceptor being linked to enhanced fusion kinetics and increased resistance to T20 (Reeves J et al., PNAS 99: 16249-16254, 2002). Higher levels of CCR5 expression on the cell surface result in more rapid membrane fusion and increased resistance to T20, whereas lower levels of coreceptor resulted in slower membrane fusion and enhanced sensitivity to T20. Thus, reductions in coreceptor expression levels prolong fusion kinetics, keeping Env in a T20 sensitive state for a longer period of time.

production was measured in the culture supernatants using a commercial p24 antigen ELISA (NCI, Frederick). Cell viability was determined using the MTT assay (Roche).

The antiviral data was then analyzed for synergy using two different methodologies, the Median Effect principle and Three Dimensional modeling. The Median Effect principle requires that the antiviral assay be designed using combinations of drug concentrations at fixed ratios. For Three Dimensional modeling analysis, combinations of drug concentrations were tested using the checkerboard design.

The antiviral effect of the RAPA/T-20 combination in the replication of HIV-1 ADA in PBMCs was investigated using Median Effect analysis and Three-Dimensional modeling. To this end, 2-fold dilutions of RAPA and T-20 were tested in the checkerboard design. RAPA was tested at concentrations ranging 0.03-1 nM and T-20 was tested in the 1.5-50 nM range. Viral replication p24 values obtained on day 7 after infection were first analyzed by the Median Effect principle using CalcuSyn software. Dose-effect relationship parameters of RAPA and T-20 alone and in combination on the replication of R5 HIV-1 in PBMCs are shown in Table 1

| Drug dose | | Fa | m | Dm | | r | CI at | | |
|---|---|---|---|---|---|---|---|---|---|
| | | | | | | | ED50 | ED75 | ED90 |
| RAPA (nM) | T-20 (nM) | | | | | | | | |
| 0.03 | | 0.017 | | | | | | | |
| 0.06 | | 0.102 | | | | | | | |
| 0.12 | | 0.114 | | | | | | | |
| 0.25 | | 0.540 | | | | | | | |
| 0.5 | | 0.620 | | | | | | | |
| 1 | | 0.880 | 1.93 | 0.31 | nM | 0.98 | | | |
| | 1.5 | 0.210 | | | | | | | |
| | 3.12 | 0.260 | | | | | | | |
| | 6.25 | 0.400 | | | | | | | |
| | 12.5 | 0.600 | | | | | | | |
| | 25 | 0.810 | | | | | | | |
| | 50 | 0.980 | 1.75 | 6.16 | nM | 0.94 | | | |
| RAPA (nM) + T-20 (nM) (1:50 ratio) | | | | | | | | | |
| 0.03 | 1.5 | 0.420 | | | | | | | |
| 0.06 | 3.12 | 0.650 | | | | | | | |
| 0.12 | 6.25 | 0.875 | | | | | | | |
| 0.25 | 12.5 | 0.890 | | | | | | | |
| 0.5 | 25 | 0.996 | | 0.042 | nM (RAPA) | | | | |
| 1 | 50 | 0.998 | 1.92 | 2.13 | nM (T-20) | 0.95 | 0.53 | 0.44 | 0.36 |

Fa = Fractional inhibition;
m = slope coefficient of the curve;
Dm = dose at 50% inhibition (equivalent to IC50 value);
r = linear correlation coefficient of the median effect plot;
CI = combination index at combination ratio RAPA/T-20 of 1/50.

In order to determine the nature and degree of interaction between RAPA and T20, infectivity assays were performed in the presence of the drugs, alone and in combination. The infectivity assays were performed using PBMCs from healthy donors. PBMCs were cultured for 7 days in the presence of IL-2 (100 U/ml) in the presence or absence of RAPA. On day 7, cells were infected by exposure to the R5 strain HIV-1 ADA (m.o.i of 0.001) for 2 h. Non-adsorbed virus was removed by 3 washes with PBS. Infected cells were then plated in RPMI-10 supplemented with IL-2 (100 U/ml) in the presence of different concentrations of RAPA and T20. Each drug concentration was tested in triplicate. Medium was changed in day 3 after infection and drugs were added at the same concentration as before. On day 7 after infection, virus When drugs were used alone, RAPA and T-20 inhibited virus replication with IC50 values of 0.31 and 6.16 nM, respectively. When the drugs were used in combination at a RAPA:T-20 ratio of 1:50, the IC50 values of RAPA and T-20 were reduced to 0.042 and 2.13 nM, respectively. These reductions in IC50 values suggested a synergistic interaction between RAPA and T-20 in antiviral activity. To further evaluate the antiviral effect of the RAPA/T-20 combination, the combination index (CI) value was calculated. The CI value determines the degree and nature of the drug interaction. CI values at 50, 75 and 90% inhibition levels of viral replication were 0.53, 0.44 and 0.36, indicating that the drug combination is synergistic.

Figure 11:
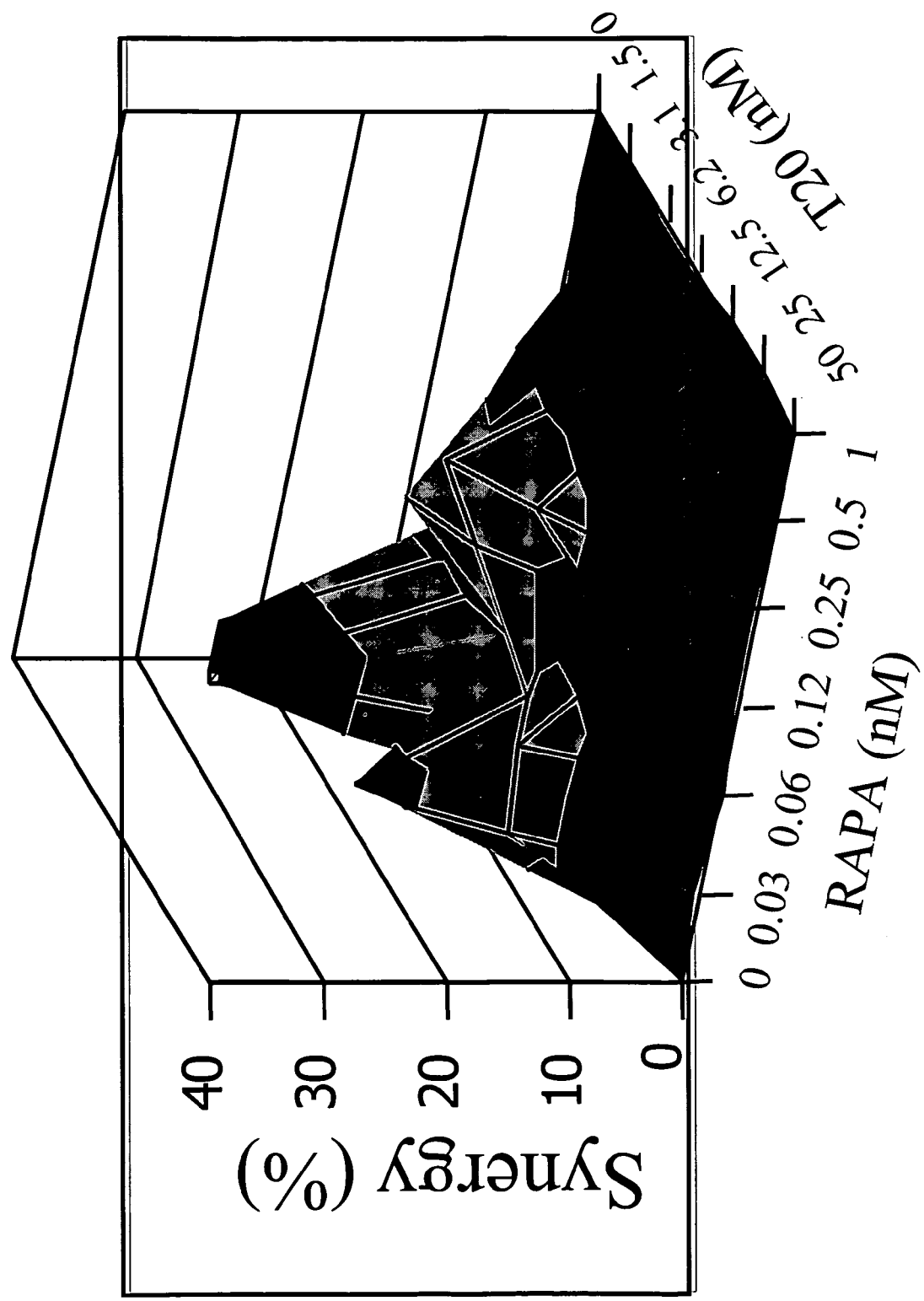
FIG. 11 shows that the combination of RAPA and T-20 is synergistic against R5 HIV-1. Three-dimensional interaction of RAPA and T-20 antiviral activity against HIV-1 ADA in PBMCs. Data was analyzed using MacSynII software. Synergy is a rise from the additive surface. 95% confidence interval plot is shown.
Figure 12:
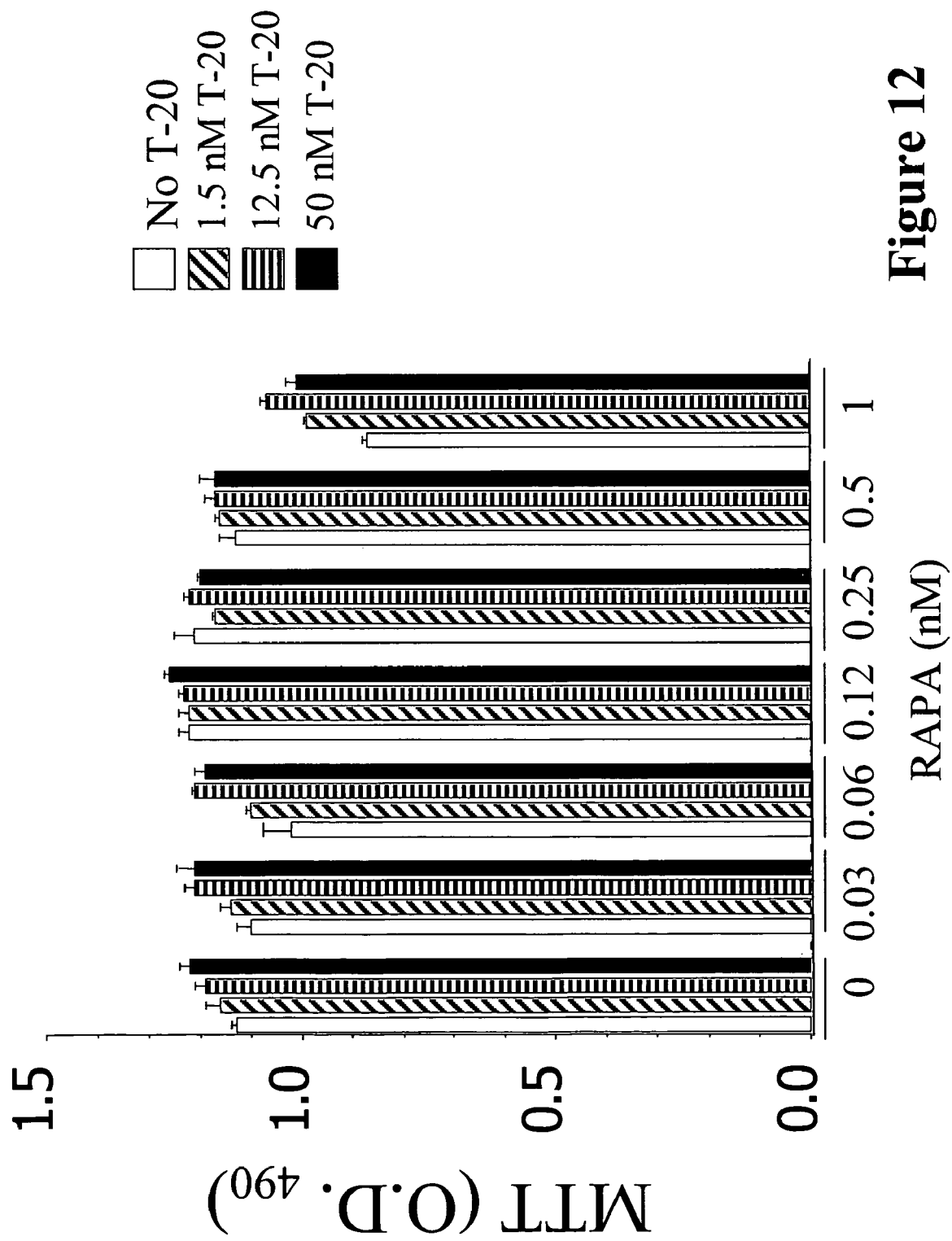
FIG. 12 shows that the combination of RAPA and T20 is not toxic to cells. PBMCs were cultured in the presence of RAPA and T20 for 7 days. Viability was determined by using the MTT assay.

The antiviral effect of the RAPA/T-20 combination was also analyzed using Three-Dimensional modeling with MacSynergy II software. This method allows analysis of the entire drug interaction surface. Results are shown in FIG. 11. Synergistic interactions were observed across the entire concentration grid with a calculated synergy volume of 253.85 (95% CL, 91-417). Assessment of cell viability by MTT indicated that the synergistic antiviral effect was not due to reduced cell viability in the RAPA/T-20 combination as shown in FIG. 12.

Example 12

Figure 13:
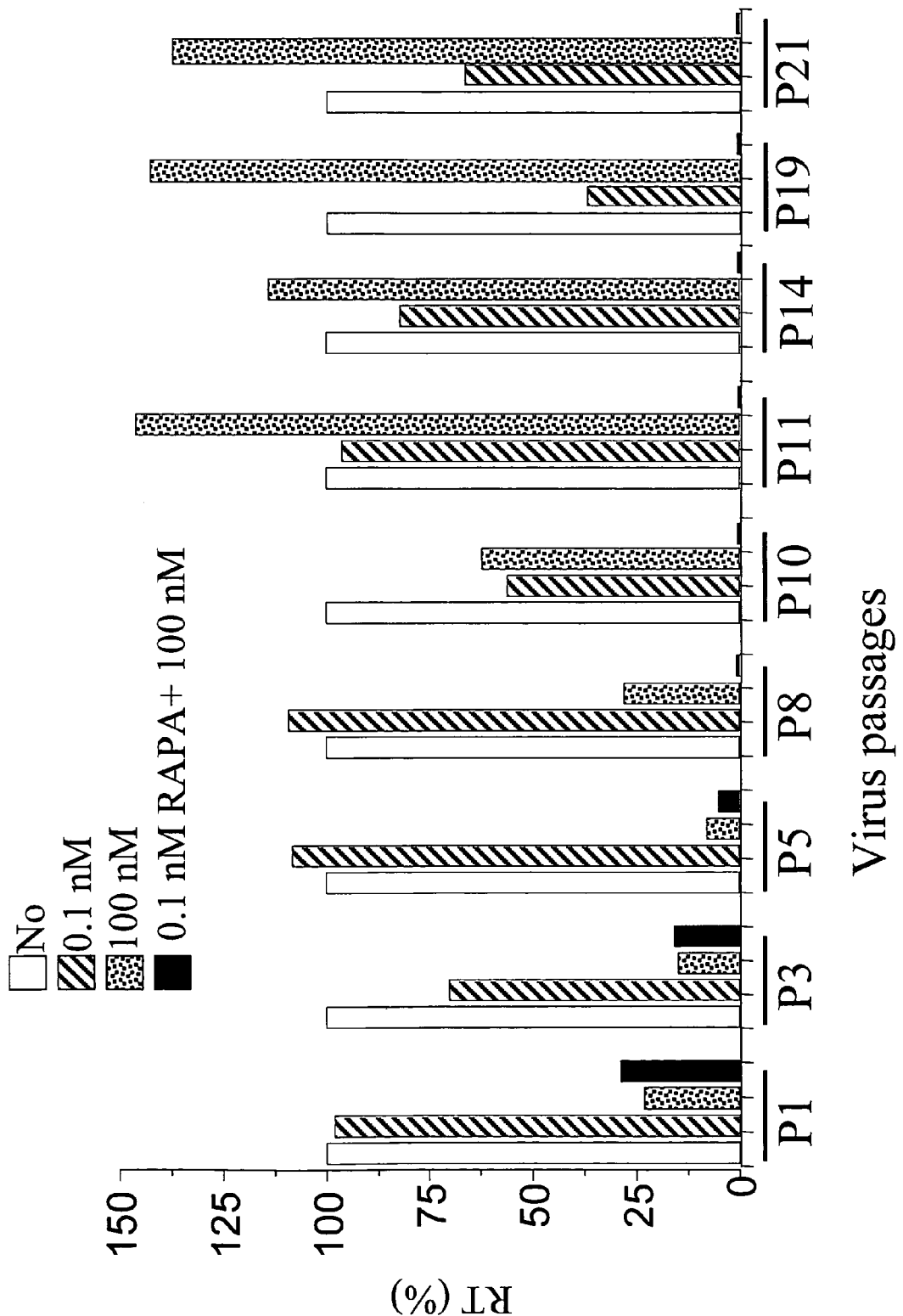
FIG. 13 shows that the RAPA/T20 combination delays emergence of resistance to T20. HIV-1 ADA was passaged in PBMCs 21 times in the presence of RAPA, T-20 or RAPA+T20. After every passage, virus content in the culture supernatant was measured using the RT assay.

HIV-1 replication in the presence of T20 leads to the emergence of drug resistant strains in vitro and in vivo, and this resistance is associated with mutations in the aa 36-45 of gp 41. Based on the synergistic antiviral activity of the RAPA/T20 combination, the impact of the drug combination versus drugs alone was assessed in the emergence of T20 resistance in vitro. To this end, HIV-1 ADA was passaged weekly for 24 weeks in the presence of RAPA, T20 and RAPA/T20 combined. During the initial 9 passages, T20 inhibited virus replication by >75%. On the $10^{th}$ passage, reduced sensitivity to T20 was observed and from the $11^{th}$ passage onwards 100 nM did not exert antiviral activity. The passage of the virus in the presence of 0.1 nM RAPA showed slightly reduced viral replication in some passages but not in others. However, when RAPA and T20 were combined, virus replication was suppressed by $\geq$70% throughout the 24 passages, as shown in FIG. 13. Thus, the RAPA/T-20 combination delays the emergence of T-20 resistance in CCR5-using HIV-1.

Example 13

Figure 14:
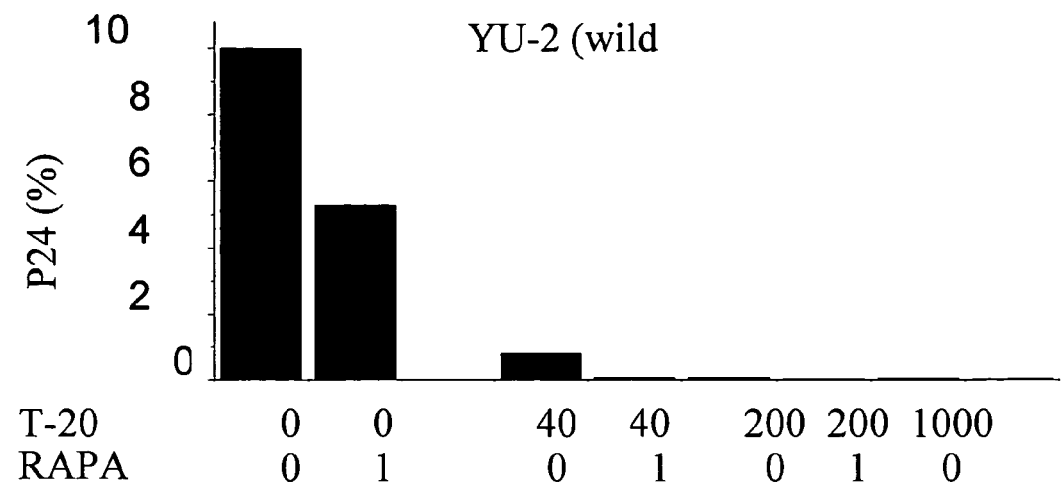
FIG. 14 shows that the RAPA/T20 combination is effective against T20 resistant R5 HIV-1. PBMCs were infected with wild type and gp41 mutant clones of HI-1 YU2. Infected PBMCs were cultured in the presence of RAPA, T20 and RAPA+T20 at the indicated concentrations. Virus growth was determined by p24 assay in the culture supernatants on day 7 after infection.
Figure 14:
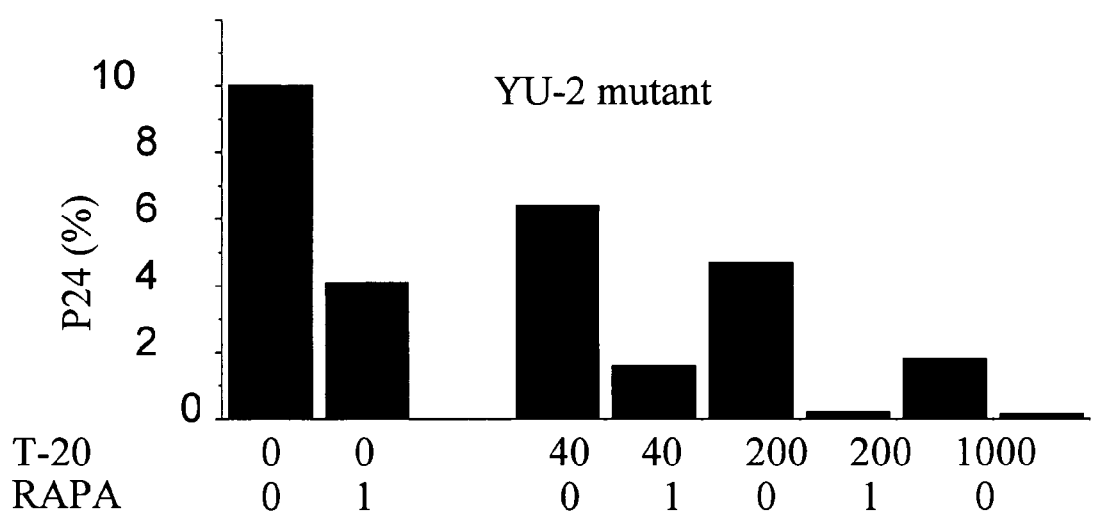
Figure 14:
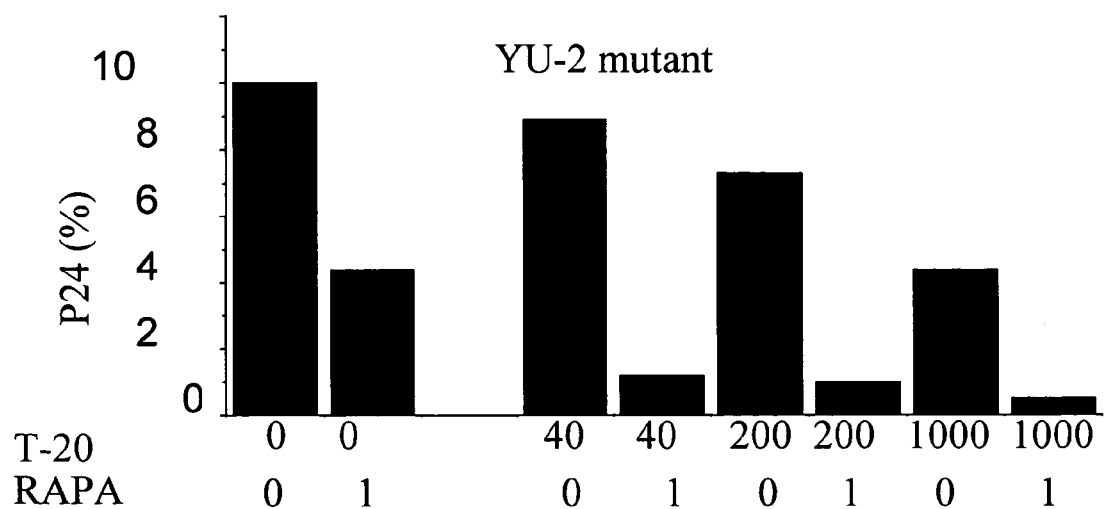

Amino acids changes in positions 36-43 of HR1 of gp41 confer resistance to T20 and they have been described both in vitro and in vivo. These mutations in HR1 reduce affinity binding for T20 but they are also likely to reduce affinity between HR1 and HR2 and therefore slow the process of fusion. It has been shown that T20 resistant mutant clones containing 36D and 38M substitutions in HR1 display slower fusion kinetics than the parental clone. Based on these observations, it was postulated that the slower fusion kinetics of these T20 mutants could be further slow down by reducing the amount of CCR5 coreceptor available, which, in turn, would prolong the window of opportunity for T20 binding. To test this hypothesis, the antiviral activity of the RAPA/T20 combination was tested on HIV-1 clone YU2 and its derivatives containing mutations in amino acid positions 36 and 43 of HR1. Results are shown in FIG. 14 and they indicate that the T20 resistant mutants are sensitive to the RAPA/T20 combination.

REFERENCES

All references cited herein are hereby incorporated by reference herein for all purposes.

Andrieu, J., Even, P. & Tourani, J. (1998) in *Autoimmune Aspects of HIV Infection*, eds. Andrieu, J.-M., Bach, J.-F. & Even, P. (R. Soc. Med. Services, London), pp. 191-194.

Baba, M., Nishimura, O., Kanzaki, N., Okamoto, M., Sawada, H., Iizawa, Y., Shiraishi, M., Aramaki, Y., Okonogi, K., Ogawa, Y., et al. (1999) *Proc. Natl. Acad. Sci. USA* 96, 5698-5703.

Baba, M., Imai, T., Yoshida, T. & Yoshie, O. (1996) *Int. J. Cancer* 66, 124-129.

Bleul, C., Wu, L., Hoxie, J., Springer, T. & Mackay, C. (1997) *Proc. Natl. Acad. Sci. USA* 94, 1925-1930.

Bjornal, A., Sonnerborg, A., Tscherning, C., Albert, J. & Fenyo, E. (1999) *AIDS Res. Hum. Retroviruses* 15, 647-653.

Calabrese, L., Lederman, M., Spritzler, J., Coombs, R., Fox, L., Schock, B., Yen-Lieberman, B., Johnson, R., Mildvan, D. & Parekh, N. (2002) *J. Acquired Immune Defic. Syndr.* 29, 356-362.

Cocchi, F., DeVico, A., Garzino-Demo, A., Arya, S., Gallo, R. & Lusso, P. (1995) *Science* 270, 1811-1815.

Dybul, M., Fauci, A., Barlett, J., Kaplan, J. & Pau, A. (2002) *Ann. Intern. Med.* 137, 381-433.

Essex, M. (1999) *Adv. Virus Res.* 53, 71-88.

Guba, M., von Breitenbuch, P., Steinbauer, M., Koehl, G., Flegel, S., Hornung, M., Bruns, C. J., Zuelke, C., Farkas, S., Anthuber, M., et al. (2002) *Nat. Med.* 8, 128-135.

Heredia, A; Amoroso, A; Davis, C.; Le, N.; Readon, E.; Klingebiel, E.; Gallo, R. C; and Redfield R. R. (2003) *Proc. Natl. Acad. Sci. USA,* 100 (18) 10411-10416.

Heredia, A., Davis, C., Amoroso, A., Dominique, J., Le, N., Klingebiel, E., Reardon, E., Zella, D. & Redfield, R. (2003) *Proc. Natl. Acad. Sci. USA* 100, 4179-4184.

Kahan, B. & Camardo, J. (2001) *Transplantation* 72, 1181-1193.

Kinter, A., Poli, G., Fox, L., Hardy, E. & Fauci, A. (1995) *J. Immunol.* 154, 2448-2459.

Lane, B., Markovitz, D., Woodford, N., Rochford, R., Strieter, R. & Coffey, M. (1999) *J. Immunol.* 163, 3653-3661.

Levine, B., Mosca, J., Riley, J., Carroll, R. G., Vahey, M. T., Jagodzinski, L. L., Wagner, K. F., Mayers, D. L., Burke, D. S., Weislow, O. S., et al. (1996) *Science* 272, 1939-1943.

Liu, R., Paxton, W., Choe, S., Ceradini, D., Martin, S., Horuk, R., MacDonald, M., Stuhlmann, H., Koup, R. & Landau, N. (1996) *Cell* 86, 367-377.

Lin, Y.-L., Mettling, C., Portales, P., Reynes, J., Clot, J. & Corbeau, P. (2002) *Proc. Natl. Acad. Sci. USA* 99, 15590-15595.

Loetscher, P., Seitz, M., Baggiolini, M. & Moser, B. (1996) *J. Exp. Med.* 184, 569-577.

Lori, F., Malykh, A., Cara, A., Sun, D., Weinstein, J. N., Lisziewicz, J. & Gallo, R. C. (1994) *Science* 266, 801-805.

Perno, C. & Yarchoan, R. (1993) in *Current Protocols in Immunology*, eds. Coligan, J. E., Kruisbeek, A. M., Margulies, D. H., Shevach, E. M. & Strober, W. (Wiley, New York), pp. 12.4.1-12.4.11.

Poli, G. & Fauci, A. (1993) in *Current Protocols in Immunology*, eds. Coligan, J. E., Kruisbeek, A. M., Margulies, D. H., Shevach, E. M. & Strober, W. (Wiley, New York), pp. 12.3.1-12.3.7.

Poon, M., Badimon, J. & Fuster, V. (2002) *Lancet* 359, 619-622.

Reeves J et al., (2002) PNAS 99: 16249-16254.

Rizzardi, G., Harari, A., Capiluppi, B., Tambussi, G., Ellefsen, K., Ciuffreda, D., Champagne, P., Bart, P., Chave, J., Lazzarin, A. & Pantaleo, G. (2002) *Clin. Invest.* 109, 681-688.

Roy, J., Sèbastien, J., Fortin, J. & Tremblay, M. (2002) *Antimicrob. Agents Chemother.* 46, 3447-3455.

Sehgal, S.-N. (1998) *Clin. Biochem.* 31, 335-340.

Simmons, G., Clapham, P., Picard, L., Offord, R. E., Rosenkilde, M. M., Schwartz, T. W., Buser, R., Wells, T. N. & Proudfoot, A. E. (1997) *Science* 276, 276-279.

Spina, C., Guatelli, J. & Richman, D. (1995) *J. Virol.* 69, 2977-2988.

Strizki, J., Xu, S., Wagner, N., Wojcik, L., Liu, J., Hou, Y., Endres, M., Palani, A., Shapiro, S., Clader, J. W., et al. (2001) *Proc. Natl. Acad. Sci. USA* 98, 12718-12723.

Trkola, A., Kuhmann, S., Strizki, J., Maxwell, E., Ketas, T., Morgan, T., Pugach, P., Xu, S., Wojcik, L., Tagat, J., et al. (2002) *Proc. Natl. Acad. Sci. USA* 99, 395-400.

Ullman, K., Northrop, J., Verweij, C. & Crabtree, G. (1990) *Annu. Rev. Immunol.* 8, 421-452.

Ward, S., Bacon, K. & Westick, J. (1998) *Immunity* 9, 1-11.

Weissman, D., Dybul, M., Daucher, M., Davey, R., Walker, R. & Kovacs, J. (2000) *J. Infect. Dis.* 181,933-938.

Willey, R., Smith, D., Lasky, L., Theodore, T., Earl, P., Moss, B., Capon, D. & Martin, M. (1988) *J. Virol.* 62, 139-147.

Zack, J., Arrigo, S., Weitsman, S., Go, A., Haislip, A. & Chen, I. (1990) *Cell* 61, 213-222.

Zella, D., Riva, A., Weichold, F., Reitz, M. & Gerna, G. (1998) *Immunol. Lett.* 62, 45-49.

That which is claimed is:

1. A pharmaceutical composition for decreasing expression of CCR5 surface receptors on mononuclear cells, the composition comprising at least one G1 phase arresting compound and at least one HIV antiviral agent that inhibits or reduces entry of HIV to mononuclear cells, wherein the G1 phase arresting compound is rapamycin and the HIV antiviral agent is T20, wherein the rapamycin and T20 are in amounts to form a synergistically effective mixture to reduce replication of HIV.

2. The pharmaceutical composition of claim 1, wherein the compound is administered orally, rectally, nasally, topically, vaginally or parenterally.

* * * * *